US008828727B2

(12) United States Patent
Marasco

(10) Patent No.: US 8,828,727 B2
(45) Date of Patent: Sep. 9, 2014

(54) LENTIVIRAL VECTORS AND USES THEREOF

(75) Inventor: Wayne A. Marasco, Wellesley, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 1034 days.

(21) Appl. No.: 11/135,235

(22) Filed: May 23, 2005

(65) Prior Publication Data

US 2006/0019395 A1    Jan. 26, 2006

Related U.S. Application Data

(60) Provisional application No. 60/589,610, filed on Jul. 21, 2004.

(51) Int. Cl.
| | | |
|---|---|---|
| C12N 15/867 | (2006.01) | |
| C40B 50/06 | (2006.01) | |
| C07K 16/18 | (2006.01) | |
| C07K 16/00 | (2006.01) | |
| C12N 15/86 | (2006.01) | |
| C12N 15/10 | (2006.01) | |
| C07K 16/28 | (2006.01) | |
| C07K 16/10 | (2006.01) | |

(52) U.S. Cl.
CPC ........ *C12N 15/1037* (2013.01); *C07K 2317/21* (2013.01); *C12N 2840/203* (2013.01); *C07K 2317/622* (2013.01); *C12N 2810/6054* (2013.01); *C07K 2319/035* (2013.01); *C07K 16/18* (2013.01); *C07K 2319/60* (2013.01); *C12N 2840/44* (2013.01); *C12N 2830/50* (2013.01); *C07K 16/00* (2013.01); *C12N 15/86* (2013.01); *C12N 2740/16043* (2013.01); *C12N 2800/30* (2013.01); *C12N 2830/48* (2013.01); *C07K 16/2866* (2013.01); *C12N 2740/16045* (2013.01); *C12N 2810/6081* (2013.01); *C07K 2319/00* (2013.01); *C12N 2830/003* (2013.01); *C07K 16/1072* (2013.01)
USPC ............................................. 435/457; 506/26

(58) Field of Classification Search
None
See application file for complete search history.

(56) References Cited

U.S. PATENT DOCUMENTS

| 5,656,465 A | 8/1997 | Panicali et al. ............ 435/172.3 |
|---|---|---|
| 5,665,577 A | 9/1997 | Sodroski et al. ............ 435/172.3 |
| 5,723,287 A * | 3/1998 | Russell et al. ..................... 435/5 |
| 6,074,836 A * | 6/2000 | Bordignon et al. ........... 435/7.24 |
| 6,218,187 B1 * | 4/2001 | Finer et al. .................... 435/457 |
| 7,252,991 B2 * | 8/2007 | Finer et al. ................. 435/320.1 |
| 2003/0044981 A1 | 3/2003 | Marasco et al. ............ 435/456 |
| 2003/0083290 A1 | 5/2003 | Kingsman et al. .............. 514/44 |
| 2005/0048578 A1 * | 3/2005 | Zhang ........................... 435/7.1 |

FOREIGN PATENT DOCUMENTS

| WO | WO-9406920 A1 | 3/1994 |
|---|---|---|
| WO | WO 94/12626 | 6/1994 |
| WO | WO-9429438 A1 | 12/1994 |
| WO | WO-9506723 A1 | 3/1995 |
| WO | WO-9528393 A1 | 10/1995 |
| WO | WO 97/14809 | 4/1997 |
| WO | WO-0112215 A2 | 2/2001 |

OTHER PUBLICATIONS

Russell et al., 1993, Retroviral vectors displaying functional antibody fragments, Nucleic Acids Research, 21(5): 1081-1085.*
Karavanas et al.,1998, Cell targeting by murine retroviral vectors, Critical Review in Oncology/Hematology, 28: 7-30.*
Sharma et al., 1996, Efficient infection of a human T-cell line and of human primary peripheral blood leukocytes with a pseudotyped retrovirus vector, PNAS 93: 11842-11847.*
Cumbers et al. (2002) "Lentiviral vectors: turning a deadly foe into a therapeutic agent" Nature Biotechnology 20(11):1129-1134.*
Trono (2000) "Lentiviral vectors: turning a deadly foe into a therapeutic agent" Gene Therapy 7(1):20-23.*
International Search Report for PCT/US05/18330, mailed Jun. 14, 2006.
Baron et al. *Meth. Enzymol.*, 327:401-421 (2000).
Brown et al. *Cell*, 49(5):603-612 (1987).
Buchholz et al. *Nat. Biotech.*, 16(7):657-662 (1998).
Choe et al. *Cell*, 114(2):161-170 (2003).
Cumbers et al. *Nat. Biotech.*, 20(11):1129-1134 (2002).
Daugherty et al. *Protein Eng.*, 12(7):613-621 (1999).
Davidson et al. *Nat. Genet.*, 3(3):219-223 (1993).
Davies et al. *Annu. Rev. Biochem.*, 59:439-473 (1990).
Fack et al. *J. Immunol. Meth.*, 206:43-52 (1997).
Geller et al. *Proc. Natl. Acad. Sci. USA*, 90:7603-7607 (1993).
Geller et al. *J. Neurochem.*, 64(2):487-496 (1995).
GenBank Accession No. AAO40783 (Sep. 17, 2003).
GenBank Accession No. AAA76671 (Sep. 27, 1995).
GenBank Accession No. BAA12995 (Dec. 25, 2002).
GenBank Accession No. AAT41729 (Feb. 1, 2006).
GenBank Accession No. P03377 (Feb. 7, 2006).
GenBank Accession No. NP_057856 (Jan. 25, 2006).
GenBank Accession No. BD015376 (Aug. 27, 2002).
GenBank Accession No. BD015377 (Aug. 27, 2002).
Gennari et al. *J. Mol. Biol.*, 335(1):193-207 (2004).
Ghattas et al. *Mol. Cell. Biol.*, 11(12):5848-5859 (1991).
Hofmann et al. *Biol. Chem. Hoppe-Seyler*, Abstract MF C-35, 374:166 (1993).
Huang et al. *Proc. Natl. Acad. Sci. USA*, 101(9):2706-2711 (2004).
Kaplitt et al. *Nat. Genet.*, 8(2):148-154 (1994).
La Salle et al. *Science*, 259:988-990 (1993).
Macejak et al. *Nature*, 353:90-94 (1991).
Martin et al. *Nature*, 415:802-806 (2002).
*J. Immunol.*, 169(20):837-846 (2002), Matthews et al.
Naldini et al. *Science*, 272:263-267 (1996).
Nielsen et al. *Protein Eng.*, 10(1):1-6 (1997).
Oh et al. *Genes Dev.*, 6(9):1643-1653 (1992).

(Continued)

*Primary Examiner* — Tracy Vivlemore
*Assistant Examiner* — Karen S Weiler
(74) *Attorney, Agent, or Firm* — Cooley LLP; Ivor R. Elrifi; Cynthia A. Kozakiewicz

(57) ABSTRACT

The invention relates to compositions containing polynucleotide vectors capable of expressing a nucleic acid encoding a fusion polypeptide on the surface of a viral particle and/or a eukaryotic cell.

10 Claims, 23 Drawing Sheets

(56) References Cited

OTHER PUBLICATIONS

Parolin et al. *J. Virol.*, 68(6):3888-3895 (1994).
Pelletier et al. *Nature*, 334:320-325 (1988).
Potrykus et al. *Mol. Gen. Genet.*, 199(2):183-188 (1985).
Presta L., *Nat. Biotech.*, 20:1096-1097 (2002).
Reczko et al. in R. Guigó and D. Gusfield (eds.), *Algorithms in Bioinformatics, Proceedings of the 2nd Int. Workshop WABI*, Rome, Italy, Sep. 17-21, Lecture in Computer Science, Springer, 2453:60-67 (2002).
Reiser et al. *Proc. Natl. Acad. Sci. USA*, 93:15266-15271 (1996).
Rider et al. *Science*, 301:213-215 (2003).
Sale et al. *Nature*, 412:921-926 (2001).
Shusta et al. *Nat. Biotechnol.*, 18:754-759 (2000).
Smith *Science*, 228:1315-1317 (1985).
Thillet et al. *J. Biol. Chem.*, 263(25):12500-12508 (1988).
Yang et al. *J. Virol.*, 69(4):2004-2015 (1995).
Yao et al. *Hum. Gene Ther.*, 9:1939-1950 (1998).
Kessels et al., "Changing T cell specificity by retroviral T cell receptor display", *PNAS*, 97(26):14578-14583 (2000).
Malmqvist, M., "Biospecific interaction analysis using biosensor technology", *Nature*, 361:186-187 (1993).
Mountford et al., "Internato ribosome entry sites and dicistronic RNAs in mammalian transgenesis", *Trends in Genetics.*, 11(5):179-184 (1995).

* cited by examiner

LENTIVIRAL VECTORS AND USES THEREOF

RELATED APPLICATION

This application claims priority to provisional patent application U.S. Ser. No. 60/589,610, filed Jul. 21, 2004, which is incorporated herein by reference in its entirety.

FIELD OF THE INVENTION

The invention relates to compositions that provide for the expression of a candidate polypeptide on the surface of a viral particle and/or a mammalian cell, and methods of use thereof.

BACKGROUND OF THE INVENTION

Antibody libraries are useful to identify antibodies of interest and to screen for novel antibody-antigen complexes. For example, the Mehta I and Mehta II single chain antibody libraries contain over 27 billion non-immune human antibodies. Previously, such libraries have been screened using phage display technology. The adaptation of antibody presentation from phage display to mammalian display requires new vector delivery systems.

Vectors that have been employed to deliver exogenous nucleic acids include both DNA viral vectors and RNA viral vectors. For example, DNA vectors include pox vectors such as orthopox or avipox vectors (see, e.g., U.S. Pat. No. 5,656,465), herpes virus vectors, such as herpes simplex I Virus (HSV) vectors (See, Geller, A. I. et al., *J. Neurochem.* 64:487 (1995); Lim, F., et al., *DNA Cloning: Mammalian Systems*, D. Glover, Ed., Oxford Univ. Press, Oxford, England (1995); Geller, A. I. et al., *Proc. Natl. Acad. Sci., U.S.A.* 90:7603 (1993); Adenovirus vectors (Legal Lasalle et al., *Sci.* 259-988 (1993); Davidson et al., *Nat. Genet.* 3:219 (1993); Yang et al., *J. Virol.*, 69:2004 (1995)); and Adeno Associated Virus Vectors (See, Kaplitt, M. G., et al., *Nat. Genet.* 8; 148 (1994)). Retroviral vectors include vectors obtained from Moloney murine leukemia viruses (MMLV) and human immunodeficiency viruses (HIV) (See, U.S. Pat. No. 5,665,577).

Various vectors have characteristics that make them desirable for certain applications. For example, a retroviral vector can be used to infect a host cell and have the genetic material integrated into that host cell with high efficiency. One example of such a vector is a modified Moloney murine leukemia virus (MMLV), which has had its packaging sequences deleted in order to prevent packaging of the entire retroviral genome. However, that retrovirus does not transduce resting cells. Additionally, since many retroviruses typically enter cells via specific receptors, if the specific receptors are not present on a cell or are not present in large enough numbers, the infection is either not possible or is inefficient. Safety issues have also been raised following outbreaks of wild-type viruses from the recombinant MMLV producing cell lines, i.e., reversions.

A vector derived from an adenovirus can infect a wide range of cells. However, the transferred genetic material is not integrated. Therefore, any expression or screening procedures are limited to the time when the transferred genetic material is episomal. Thus, studies can only occur for a relatively short period of time.

Recently, attention has focused on lentiviral vectors such as those based upon the primate lentiviruses, e.g., human immunodeficiency viruses (HIV) and simian immunodeficiency virus (SIV). By using a pseudotyped vector (i.e., one where an envelope protein from a different species is used), problems encountered with infecting a wide range of cell types can be overcome by selecting a particular envelope protein based upon the type of cell to be infected. Additionally, in view of the complex gene splicing patterns seen in lentiviruses such as HIV, multivalent vectors (i.e., those expressing multiple genes) having a lentiviral core, such as an HIV core, are expected to more efficiently express nucleic acids of interest.

The use of lentiviral vectors, such as those based on primate lentiviruses, (e.g., HIV and SIV), to perform large-scale mammalian transfections offers several advantages over retroviral vectors. Lentiviral vectors containing genes encoding antibodies can infect quiescent cells and proliferating cells both in vivo and in vitro. (See, Reiser et al., PNAS 93:15266-15271 (1996); Naldini et al., Science 272:263-267 (1996)). Additionally, lentiviral vectors allow constitutive or induced expression of heterologous polypeptides, thus providing for the production of antibodies in culture and in animal.

In recent years, attention has been directed to developing large libraries typically consisting of monoclonal antibodies or peptides. For example, antigen binding antibody fragments have been expressed on the surface of filamentous phage (G. P. Smith, Science 228: 1315 (1985)), and used to create large libraries of such antibodies—e.g., $10^7$ members or more, referred to as phage display libraries. In phage display libraries, the carboxyl-terminal end of the Fd or Fv region is tethered to a fragment of a phage coat protein, which anchors, for example, Fab fragment to the surface of the phage. Antibody display systems have been described in non-mammalian cells, such as *E. coli* (Daugherty et al, Protein Eng 1999, 12:613-621), yeast (Shusta et al. Nat Biotechnol 2000, 18:754-759), and baculoviral infection of Sf9 insect cells. Despite the advantages of being able to express antibodies on the surface of phage or non-mammalian cells, it was recognized that the expressed antibodies can often fail to fully retain their binding activity (Choe et al. Cell 2003, 114; 161-170; Huang et al. PNAS 2004, 101:2706-2711).

SUMMARY OF THE INVENTION

The invention is based in part on the discovery of compositions and methods that provide for the display of candidate polypeptides such as an antibody or fragment thereof on the surface of a mammalian cell or viral particle.

The methods of the invention employ a viral display vector containing a nucleic acid sequence encoding a fusion protein. The fusion protein contains a leader peptide, a candidate polypeptide, a portion of an immunoglobulin molecule and a transmembrane moiety. Optionally, the fusion protein further contains an envelope incorporation signal, which is a polypeptide sequence that directs the expression of the candidate polypeptide to the surface (or envelope, env) of the viral particle.

Suitable candidate polypeptides include, but are not limited to, monoclonal antibody variable regions, single chain antibodies, domain antibodies, diabodies, or Fab antibodies. The candidate polypeptide may be derived from a library, such as a human single-chain antibody library (e.g., the Mehta I or Mehta II libraries), a natural peptide library, or a random peptide library.

The portion of the immunoglobulin molecule contains a domain of the constant region of an Ig molecule or functional fragment thereof. For example, the immunoglobulin molecule may contain the hinge, CH2 and CH3 region of an IgG molecule The transmembrane moiety includes, a viral transmembrane moiety or mammalian transmembrane moiety. For example, transmembrane moiety is the lentiviral gp41, CD28, CD8 or IgM transmembrane moiety or a functional fragment thereof.

The fusion protein is operably linked to a constitutive promoter or an inducible promoter. Constitutive promoters include CMV. SV40, or CDK9. Inducible promoters include for example a tetracycline inducible promoter, an alcohol inducible promoter, a steroid inducible promoter, a metal inducible promoter, a light inducible promoter, or a temperature inducible promoter.

The various aspects the viral display vector contains one or more additional nucleic aid sequence such as a selectable marker or toxin. Selectable markers include for example as green fluorescent protein, a red fluorescent protein, a yellow fluorescent protein, a blue fluorescent protein, a ferredoxin IV protein, a member of the luciferase family, or a member of the aequorin family.

The viral display vector is a lentiviral vector, including, but not limited to, vectors obtained from human immunodeficiency virus (HIV), simian immunodeficiency virus (SIV), equine infectious anemia virus (EIAV), visna virus, caprine arthritis-encephalitis virus (CAEV), bovine immune deficiency virus (BIV), bovine leukemia virus (BLV), and feline immunodeficiency virus (FIV).

A candidate polypeptide is displayed on the surface of a mammalian cell by contacting a packaging cell with a viral display vector that contains a nucleic acid sequence encoding a fusion protein under conditions such that the packaging cell generates one or more viral particles containing the nucleic acid sequence encoding the fusion protein. Optionally, the candidate polypeptide is expressed on the surface of the viral particle. The viral particles are contacted with a mammalian display cell under conditions sufficient to express the fusion protein in the mammalian cell such that it is displayed on the surface of the mammalian cell.

The packaging cell may further include a helper vector that contains one or more viral structural genes, e.g., gag, pol, tat, and/or rev and an envelope vector that contains an env gene, e.g., a vesicular stomatitis virus glycoprotein gene encoding a functional envelope protein that is operably linked to a promoter and a polyadenylation sequence.

Packaging cells include for example, BHK, VERO, HT1080, 293, 293T, RD, COS-7, CHO, Jurkat, HUT, SUPT, C8166, MOLT4/clone8, MT-2, MT-4, H9, PM1, CEM, myeloma cells (e.g., SB20 cells) and CEMX174 cells. Mammalian cells include for example, human B-cell lines such as Ramos Burkitt's lymphoma cells. In other embodiments, the cells are BHK, VERO, HT1080, 293, 293T, RD, COS-7, CHO, Jurkat, HUT, SUPT, C8166, MOLT4/clone8, MT-2, MT-4, H9, PM1, CEM, myeloma cells (e.g., SB20 cells) and CEMX174 cells.

Candidate polypeptides that bind to a target antigen are identified by contacting the viral particles with one or more mammalian display cells, under conditions such that the mammalian display cells each generate a single species of candidate polypeptide displayed on the surface of the cell. The mammalian cells displaying the single species of candidate polypeptide on the surface of the mammalian cell are separated (i.e., sorted) from mammalian cells not expressing a candidate polypeptide. The sorted mammalian cells are contacted with a target antigen to select cells that bind the target antigen. The sorting and antigen binding steps are repeated one or more times. In various aspects of the invention, the mammalian cells are contacted with a decreasing concentration of the target antigen thus enriching and affinity maturing the candidate polypeptide that binds to the target antigen.

The mammalian display cell may further contain a nucleic acid sequence encoding a calcium-sensitive bioluminescent protein, such as the aequorin protein from *Aequoria Victoria* jellyfish. In embodiments of the invention the fusion protein, when bound by target antigen, increases intracellular calcium, which causes the aequorin to emit light. (See Rider et al., 2003 Science 301:213-15.) To facilitate intracellular calcium increase, the transmembrane and intracellular domains of an immunoglobulin receptor (e.g., an IgM immunoglobulin receptor).

A soluble candidate polypeptide is produced flanking transmembrane moiety with a loxP site and inserting a second nucleic acid sequence encoding cre recombinase operably linked to an inducible promoter into the viral display vector. Exemplary loxP sites include, ATAACTTCGTATAGCATA-CATTATACGAAGTTA (SEQ ID NO: 12), expressed as a polypeptide as ITSYSIHYTKL (SEQ ID NO: 13).

The invention further provides vector systems containing any of the viral display vectors of the invention; an envelope vector containing an env gene, operably linked to a promoter and a polyadenylation sequence, encoding a functional envelope protein; and a helper vector comprising one or more viral structural genes. Optionally, the vector system may also include a cre vector that contains a nucleic acid sequence encoding cre recombinase polypeptide operably linked to an inducible promoter.

The invention also provides a viral targeting vector containing a nucleic acid encoding a fusion protein that contains a leader peptide, a candidate polypeptide, a portion of an immunoglobulin molecule and a transmembrane moiety flanked by a loxP site, a nucleic acid encoding a toxin, sequence encoding cre recombinase polypeptide, a nucleic acid encoding an entry moiety. An entry moiety is a viral envelope protein that has fusogenic activity. Preferably, the entry moiety does not have binding activity. For example, the entry moiety is a binding defective influenza hemagglutinin protein or fragment thereof, or a VSV-G protein or fragment thereof. Optionally, the viral targeting vector may also contain a nucleic acid sequence encoding a selectable marker.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
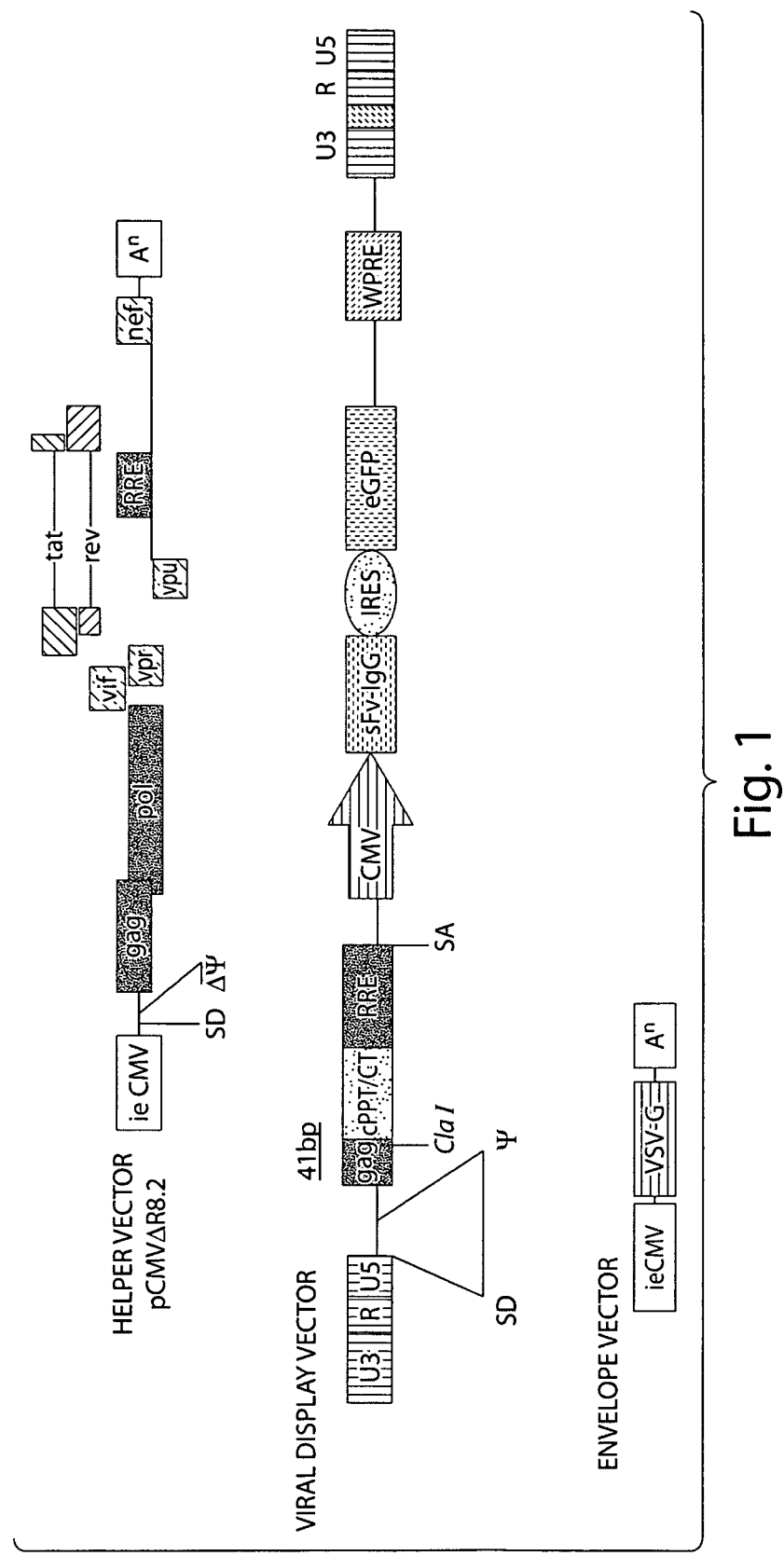
FIG. 1 is a schematic representation of exemplary viral display vectors, helper vectors and envelope constructs of the invention.
Figure 2:
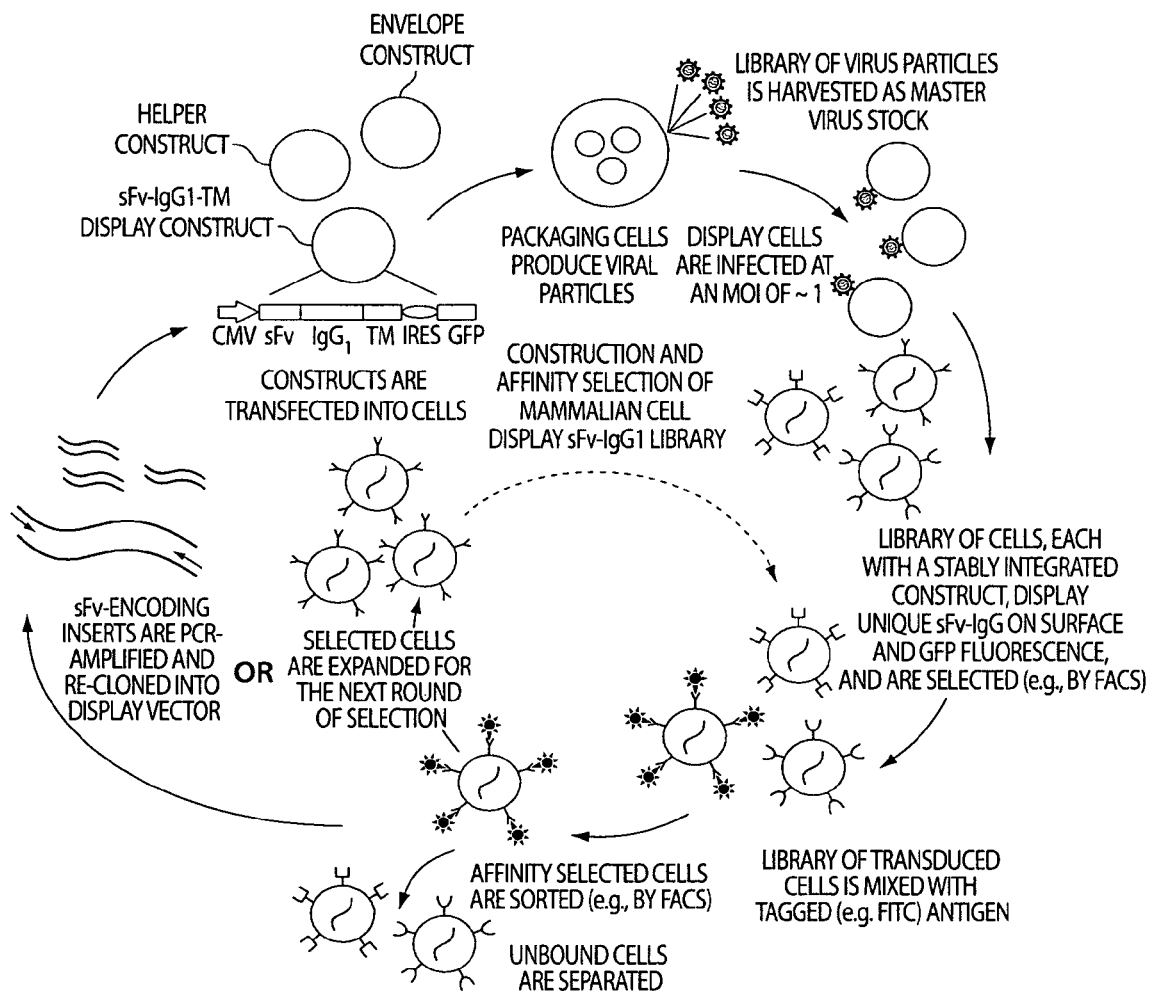
FIG. 2 is a schematic representation of the process for selection of a candidate polypeptide using mammalian cell display of candidate polypeptides.
Figure 3:
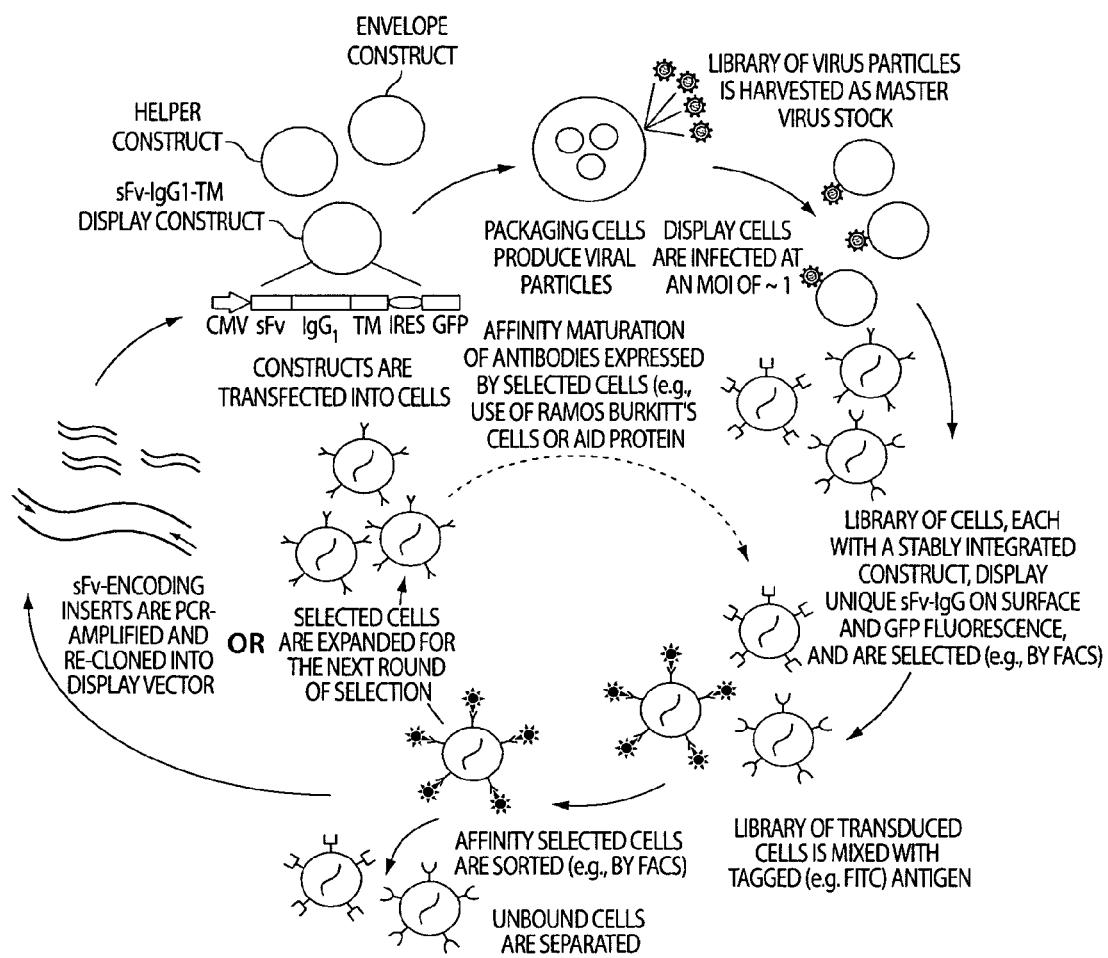
FIG. 3 is a schematic representation of the process for affinity maturation of candidate polypeptides using mammalian cell display of candidate polypeptides.

This invention provides methods and compositions for displaying a candidate polypeptide on the surface of a viral particle (i.e. virion) or a eukaryotic cell, e.g., mammalian cell. The methods and compositions of the invention employ a viral display vector containing a nucleic acid sequence encoding a fusion protein containing the candidate polypeptide. The vector is introduced into a packaging cell such that the packaging cell generates one or more viral particles containing nucleic acid encoding the fusion protein and displaying the candidate polypeptide on the surface of the particle. A mammalian display cell is contacted with the viral particles such that the mammalian cell expresses (i.e., transiently or stably) the fusion protein such that the candidate polypeptide is displayed on surface of the cell.

The expression of candidate polypeptides on the surface of a mammalian cell has a number of advantages over other expression modalities, such as E. coli, yeast, and baculoviral infection of Sf9 insect cells. For example, the candidate polypeptide produced in mammalian cells contain post-translational modifications, such as glycosylation and sulfation, that are not made in these other expression systems. Moreover, correct protein folding is increased in mammalian cells as compared to cells that lack chaperone proteins and other cellular components that increase correct folding. Additionally, the candidate polypeptides are free of bacterial, yeast or baculovirus contaminants The methods of the invention are useful, for example, to screen libraries containing nucleic acids encoding polypeptides in order to identify candidate polypeptide that binds a target antigen.

Viral Display Vectors

A viral display vector of the invention is a nucleic acid vector capable of expressing, constitutively or upon induction, a fusion protein. For example, the viral display vector is a lentiviral vector. Lentivirus vectors include, for example, a human immunodeficiency virus (HIV) (e.g, HIV-1 and HIV-2), simian immunodeficiency virus (SIV), equine infectious anemia virus (EIAV), visna virus, caprine arthritis-encephalitis virus (CAEV), bovine immune deficiency virus (BIV), bovine leukemia virus (BLV), or feline immunodeficiency virus (FIV).

A preferred lentiviral vector is obtained from HIV-1. HIV-1 vectors have been demonstrated to stably transduce non-dividing cells in vitro (See, J. Reiser et al., *Proc. Natl. Acad. Sci. USA*, 93:15266-15271 (1996)) and in vivo See, L. Naldini et al., *Science*, 272:263-267 (1996)). Thus, these vectors are capable of long-term expression. A list of suitable viruses and the cells infected thereby is provided in U.S. Patent Application 2003/0044981, the contents of which are incorporated herein by reference in its entirety.

The nucleic acid sequence encoding the fusion protein is generally under the control of a regulatory element. By "regulatory element" is meant a nucleic acid sequence sufficient to direct transcription. Regulatory elements include, for example, promoters. Regulatory elements are constitutive or inducible, and may be coupled to additional sequences or "elements," which render promoter-dependent gene expression cell-type specific, tissue-specific or inducible by external signals or agents. Such elements may be located in the 5' or 3' region of the native gene, or within an intron.

The regulatory element is operably linked to the fusion protein. By "operably linked" is meant that a coding sequence and a regulatory sequence(s) are connected in such a way as to permit gene expression when the appropriate molecules (e.g., transcriptional activator proteins) are bound to the regulatory sequence(s).

Suitable constitutive promoters include, e.g., SV40, CMV, CDK9, PGK, and ubiquitin C. An exemplary CMV promoter sequence is GenBank Accession numbers BD015376 and BD015377.

An inducible promoter system includes the tetracycline repressor (tetR), wherein expression of the nucleic acid encoding the fusion proteins of the invention is dependent on the activity of an inducible transcriptional activator. (See, Yao et al., Human Gene Therapy 9:1939-1950 (1998). (See, Baron et al. Tet repressor-based system for regulated gene expression in eukaryotic cells: Principles and advances. *Methods Enzymol* 327: 401-21(2000)).

The tet expression system includes Tet-On and Tet-Off systems. In the Tet-On system, transcription is active in the presence of the tetracycline (Tc) derivative doxycycline (Dox). Conversely, in the Tet-Off system, transcription is inactive in the presence of tetracycline or Dox. In the Tet-Off expression system, a tetracycline-controlled transactivator protein (tTA), which is composed of the Tet repressor DNA binding protein (TetR) from the Tc resistance operon of *Escherichia coli* transposon Tn10 fused to the strong transactivating domain of VP16 from Herpes simplex virus, regulates expression of a target gene that is under transcriptional control of a tetracycline-responsive promoter element (TRE). The TRE is made up of Tet operator (tetO) sequence concatamers fused to a minimal promoter (commonly the minimal promoter sequence derived from the human cytomegalovirus (hCMV) immediate-early promoter). In the absence of Tc or Dox, tTA binds to the TRE and activates transcription of the target gene. In the presence of Tc or Dox, tTA cannot bind to the TRE, and expression from the target gene remains inactive.

The Tet-On system is based on a reverse tetracycline-controlled transactivator, rtTA. Like tTA, rtTA is a fusion protein comprised of the TetR repressor and the VP16 transactivation domain; however, a four amino acid change in the tetR DNA binding moiety alters rtTA's binding characteristics such that it can only recognize the tetO sequences in the TRE of the target transgene in the presence of the Dox effector. Thus, in the Tet-On system, transcription of the TRE-regulated target gene is stimulated by rtTA only in the presence of Dox.

Alternatively, the inducible promoter system is the lac repressor system from *E. coli*. (See, Brown et al., Cell 49:603-612 (1987). The lac repressor system functions by regulating transcription of nucleic acids having mammalian cell promoters that contain the lac operator (lacO), a nucleic acid sequence to which the lac repressor (lacR) binds, preventing transcription of the target nucleic acids regulated by the lacO-containing promoter. Expression of the target nucleic acids is induced by isopropyl-β-D-thiogalactopyranoside (IPTG) treatment. For example, 293T cells are transfected with a lentiviral display vector containing a nucleic acid encoding an antibody fusion protein and a nucleic acid encoding eGFP, both of which are under the control CMV promoter having a lacO, e.g., by electroporation. The induction levels of antibodies is examined before and after IPTG treatment (0.5 mmol/L) by Western blot analysis or other measurement techniques known in the art.

Other inducible systems include FK506 dimer, VP 16 or p65 using estradiol, RU486, diphenol murislerone, rapamycin, and the ecdysone inducible system.

Organ/tissue-specific promoter include, for example, the prion protein promoter or the neuron-specific enolase promoter, the CaMKII-alpha promoter, the LAP promoter, the Clara cell 10-kD protein (CC 10) promoter can be used for lung-specific expression, the Mouse mammary tumor virus long terminal repeat, the human keratin 14 (K14) promoter, the bovine keratin 6 (K6) promoter/regulatory region, the Tek or Tie promoter and the whey acidic protein (WAP) promoter or the β-lactoglobulin promoter.

Optionally, the viral display vectors of the present invention contain a selectable marker. In general, any gene encoding a gene product that allows for selection of the cell carrying the display vector can be used as the selectable marker. Such selection systems are well known in the art and include genes that change the sensitivity of a cell to a stimulus such as a nutrient, or an antibiotic. Examples of selectable markers include, but are not limited to, known genes encoding resistance to antibiotics such as the aminoglycoside antibiotics (including, e.g., neomycin, hygromycin, kanamycin, bleomycin, and G418). (See, e.g., Potrykus et al., Mol. Gen. Genet. 199:183-188 (1985). Other selectable markers include the dihydrofolate reductase (DHFR) gene, which confers resistance to methotrexate (See, Thillet et al., J. Biol. Chem. 263:12500-12508 (1988). Other selectable markers are genes that express proteins that directly or indirectly produces light, either constitutively or upon being contacted with a compound. For example, other selectable markers include, green fluorescent protein, red fluorescent protein, yellow fluorescent protein, blue fluorescent protein, ferredoxin IV, LacZ, members of the luciferase family, or members of the aequorin family.

The selectable marker is linked to the candidate polypeptide by the use of an internal ribosome entry site (IRES) (see Marasco et al., PCT/US96/16531). The presence of an IRES sequence directs the nearly simultaneous production of the fusion protein and the selectable marker, if present. This nearly simultaneous co-expression allows for the selection of cells expressing the fusion protein based on detection of the selectable marker. IRES sequences are known in the art and include those from encephalomyocarditis virus (EMCV) (Ghattas, I. R. et al., Mol. Cell Biol., 11: 5848-5849 (1991)); BiP protein (Macejak and Samow, Nature, 353:91 (1991)); the Antennapedia gene of *Drosophila* (exons d and e) (Oh et al., Genes & Dev., 6: 1643-1653 (1992)); those in polio virus (Pelletier and Sonenberg, Nature 334:320325 (1988); see also Mountford and Smith, TIG, 11:179-184 (1985)).

The lentiviral display vector may also contain additional nucleotide sequences, including a portion of the gag gene ("gag", which allows the transduction of dividing and non-dividing cells), e.g., about 41 nucleotides at the 5' end of the gag gene bounded by a Cla I site (see, e.g., FIG. 1), which has been demonstrated to contain the RNA packaging signal and is generally sufficient for gene transfer. (See, Parolin et al., 1994 J. Virol. 68:3888-95.) The lentiviral display vector may also contain a cis-acting woodchuck hepatitis virus postregulatory regulatory element (WPRE) that post-transcriptionally stimulate transgene expression; and the viral LTR sequences R and U5, which control transcription of the vector, carry the polyadenylation signal, and integrate the virus into the genome, respectively. The WPRE is particularly useful to enhance expression of fusion proteins when an inducible promoter is used. Typically, the U3 region (self-inactivation) and all HIV-1 accessory genes are deleted. Further, the cPPT/CTS (central polypurine track) region is added. The lentiviral display vector contains a nucleic acid sequence encoding an envelope protein. Alternatively, the lentiviral display vector does not contain a nucleic acid sequence encoding an envelope protein, and protein is provided on a separate vector. Optionally, the viral particles are pseudotyped having a envelope protein that differs form the lentiviral capsid. By appropriate selection of envelope proteins one can "infect" virtually any cell. Thus, the vector can readily be targeted to a specific cell. For example, one can use an env gene that encodes an envelope protein derived from the influenza virus, VSV-G, a member of the alpha viruses (Semliki forest virus, Sindbis virus), a member of the arenaviruses (lymphocytic choriomeningitis virus), a member of the flaviviruses (tick-borne encephalitis virus, Dengue virus), a member of the rhabdoviruses (vesicular stomatitis virus, rabies virus), or a member of the orthomyxoviruses (influenza virus). Other envelopes are derived from Moloney Leukemia Virus such as MLV-E, MLV-A and GALV. Also, specific envelopes are selected in order to target the construct to a desired host cell or tissue, such as brain or vascular endothelium.

Numerous modifications can be made to the vectors, which are used to create the particles to further minimize the chance of obtaining wild type revertants. These include deletions of the U3 region of the LTR, tat deletions and matrix (MA) deletions.

An exemplary lentiviral display vector is shown in schematic form in FIG. 1. In this figure, the fusion protein, represented as "sFv-IgG," is under the control of a cytomegalovirus promoter ("CMV"). A selectable marker (e.g., eGFP) is provided downstream of an internal ribosome entry site (IRES) (See, Marasco et al., PCT/US96/16531).

The lentiviral virion (particle) is expressed by a vector system encoding the necessary viral proteins to produce a virion (viral particle). For example, the packaging cell is further transduced with one or more additional vectors encoding all the necessary viral protein to produce the viral particle. Additional vectors include a helper vector containing one or more viral structural genes. Preferably, there is at least one vector containing a nucleic acid sequence encoding the lentiviral pol proteins necessary for reverse transcription and integration, operably linked to a promoter. Preferably, the pol proteins are expressed by multiple vectors. There is also a vector containing a nucleic acid sequence encoding the lentiviral gag proteins necessary for forming a viral capsid operably linked to a promoter. Preferably, this gag nucleic acid sequence is on a separate vector than at least some of the pol nucleic acid sequence, still more preferably it is on a separate vector from all the pol nucleic acid sequences that encode pol proteins.

The gag, pol and env vector(s) do not contain nucleotides from the lentiviral genome that package lentiviral RNA, referred to as the lentiviral packaging sequence. In HIV this region corresponds to the region between the 5' major splice donor and the gag gene initiation codon (nucleotides 301-319).

The vector(s) forming the particle preferably do not contain a nucleic acid sequence from the lentiviral genome that expresses an envelope protein. Preferably, a separate vector (i.e., an envelope vector that contains a nucleic acid sequence encoding an envelope protein operably linked to a promoter is used. This env vector also does not contain a lentiviral packaging sequence. The envelope protein is from the lentivirus from which the lentiviral display vector is derived. Alternatively, the envelope protein is not from the lentivirus from which the lentiviral display vector is derived but is derived from a different virus. The resultant viral particle is referred to as a pseudotyped particle.

As shown in FIG. 1, helper construct pCMVdR8.2 contains the gag, pol, tat, and rev genes under the control of the ieCMV promoter. The gag gene encodes for the viral matrix, capsid and nucleocapsid polypeptides. The pol gene encodes for the viral reverse transcriptase and integrase enzymes. The tat gene induces viral gene expression and protein synthesis. The rev gene regulates expression of the gag, pol and env genes.

As shown in FIG. 1, the envelope vector contains the G protein of vesicular stomatitis virus ("VSV-G"), operably linked to the ieCMV promoter and A" (a polyadenylation sequence). The immediate-early CMV (ieCMV promoter; also known as CMVie) can contain a tetracycline operator downstream of the CMV promoter's TATA element. Other useful envelope proteins include those from the Moloney Leukemia Virus, such as MLV-E, MLV-A and GALV. Other env polypeptides are selected depending upon the host cell. Fragments of env polypeptides that retain cellular binding properties are also provided. For example, the HIV gp160 precursor is processed to form gp120 and gp41.

Introduction of a viral display vector, an envelope vector and a helper vector into a packaging cell) is useful, i.e., to produce a viral particle containing a nucleic acid encoding the fusion protein of the invention. Alternatively, a portion (or all) of the envelope vector and/or helper vector nucleic sequences can be contained within the viral display vector.

Suitable packaging include any cells capable of generating a lentiviral particle. Packaging cells include primary cells, embryonic stem cells and cell lines. Preferred packaging cells include for example, BHK, VERO, HT1080, 293, 293T, RD, COS-7, CHO, Jurkat, HUT, SUPT, C8166, MOLT4/clone8, MT-2, MT-4, H9, PM1, CEM, myeloma cells (e.g., SB20 cells) and CEMX174 cells. Such cell lines are available, for example, from the A.T.C.C., Manassas Va.

Fusion Proteins

A fusion protein contains a leader peptide, a candidate polypeptide, at least a portion of an immunoglobulin molecule and a transmembrane moiety. Optionally, the fusion protein contains an envelope incorporation signal. The leader peptide, candidate polypeptide, the portion of the immunoglobulin molecule and the transmembrane moiety is operably linked. By "operably-linked" is intended to mean that the nucleotide sequences of interest are in a manner that allows for expression of the nucleotide sequence (e.g., in a host cell when the vector is introduced into the host cell). Preferably, nucleic acid encoding the leader peptide is operably linked to the nucleic acid encoding the candidate polypeptide that is operably linked to the nucleic acid of the transmembrane moiety.

As used herein, the term "fusion protein" includes a polypeptide containing all or a portion of the amino acid sequences of two or more proteins. The terms "protein" and "polypeptide" are used interchangeably herein. The term "portion" includes any region of a polypeptide, such as a fragment (proteolytically or otherwise obtained) or a domain (a region of a polypeptide having an activity, such as, e.g., enzymatic activity or antigen- or DNA-binding) that contains fewer amino acids than the full-length polypeptide. Those skilled in the art will recognize that the terms "portion" and "fragment" are also used interchangeably herein.

Leader Peptide

A leader peptide includes a peptide that direct a newly synthesized protein in the ribosome to the Golgi complex for transport to the plasma membrane or out of the cell. (See, Nielsen et al., "Identification of prokaryotic and eukaryotic signal peptides and prediction of their cleavage sites" Protein Engineering, vol. 10 no. 1 pp. 1-6, 1997). Leader polypeptides are also known as signal peptides or signal polypeptides. Leader peptides generally include a string of hydrophobic amino acids. Leader peptides include an immunoglobulin leader sequence, polyhistidine or polyvaline sequences, as well as others known to those skilled in the art. Exemplary leader peptides are provided in Table 1.

Leader peptides include peptides having three regions: an n-region, which is a positively charged region at the N-terminus of the signal peptide (the "left end" of the sequence); an h-region having a hydrophobic core, optionally in the middle of the signal peptide; and a c-region, a generally polar region at the C-terminus of the leader sequence with generally small and neutral amino acids at position-1 and -3.

Leader peptides of the invention include peptides capable of being acted upon by signal peptidase, a specific protease located on the cisternal face of the endoplasmic reticulum. Leader polypeptides of the present invention also include polypeptides identified using the SIGFIND program, which predicts signal peptides at the start of protein sequences and searches open reading frames with a potential signal peptide coded in nucleotide sequences. (See, "Finding Signal Peptides in Human Protein Sequences using Recurrent Neural Networks" (2002) Reczko et al., In R. Guigo and D. Gusfield (eds.): Algorithms in Bioinformatics, Proceedings of the 2nd Int. Workshop WABI 2002, Rome, Italy, September 16-21, Lecture Notes in Computer Science, Springer, Volume 2452, pp. 60-67).

The SIGFIND program provides a score (the sig.pep score, which ranges from 0 (no signal peptide) to 9 (maximum score for presence of a signal peptide)) along the sequence that indicates the location and size of the signal peptide. Generally, a decrease in the sig.pep score from higher to lower indicates the approximate position of the signal peptide cleavage site.

TABLE 1

Ig-kappa chain leader sequence:
Met-Glu-Thr-Asp-Thr-Leu-Leu-Leu-Trp-Val-Leu-Leu-
Leu-Trp-Val-ProGlySerThrGlyAsp (SEQ ID NO: 2)

Bacteriophage T7 gene 10 leader protein:
Met-Ala-Ser-Met-Thr-Gly-Gly-Gln-Gln-Met-Gly
(SEQ ID NO: 3)

Tandem polyvaline heptad repeats:
(Val-Val-Val-Val-Val-Val)$_n$ (SEQ ID NO: 4)

Preproalbumin:
Met-Lys-Trp-Val-Thr-Phe-Leu-Leu-Leu-Leu-Phe-Ile-
Ser-Gly-Ser-Ala-Phe-Ser (SEQ ID NO: 5)

Pre-IgG light chain:
Met-Asp-Met-Arg-Ala-Pro-Ala-Gln-Ile-Phe-Gly-Phe-
Leu-Leu-Leu-Leu-Phe-Pro-Gly-Thr-Arg-Cys
(SEQ ID NO: 6)

Prelysozyme:
Met-Arg-Ser-Leu-Leu-Ile-Leu-Val-Leu-Cys-Phe-Leu-
Pro-Leu-Ala-Ala-Leu-Gly (SEQ ID NO: 7)

Acetylcholine receptor gamma subunit precursor:
Met-Val-Leu-Thr-Leu-Leu-Leu-Ile-Ile-Cys-Leu-Ala-
Leu-Glu-Val-Arg-Ser (SEQ ID NO: 8)

ER signal peptide:
$X_1$-Leu-Leu-Leu-Val-Gly-Ile-Leu-Phe-Trp-Ala-$X_2$.
(SEQ ID NO: 9)

$X_1$ may be any one or more amino acids or nothing.
$X_2$ is the remainder of the polypeptide.

Candidate Polypeptide

A candidate polypeptide is any polypeptide or fragment thereof in which expression on the surface of a viral capsid or mammalian cell is desired. A candidate polypeptide is a native a cell surface polypeptide. Alternatively, a candidate polypeptide is not a native cell surface polypeptide. The candidate polypeptide is an antibody or fragment thereof, a toxin, a hormone, a growth factor, a receptor, or a signaling molecule.

As used herein, the term "antibody" or "functional fragment thereof" refers to immunoglobulin molecules and immunologically active portions of immunoglobulin (Ig) molecules, i.e., molecules that contain an antigen binding site that specifically binds (immunoreacts with) an antigen. Such antibodies include, polyclonal, monoclonal, chimeric, and single chain fragments and $F_{ab}$, $F_{ab'}$, $F_{(ab')2}$, and an $F_{ab}$ expression library.

By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

As used herein, the terms "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides are quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473).

The candidate polypeptide can be obtained from a library. Preferred libraries include human single-chain antibody libraries, natural peptide libraries, and random peptide libraries. Exemplary libraries include the Mehta I and Mehta II phage display libraries. (See, Gennari et al., J. Mol. Biol. 335(1):193-207 (2004)). The Mehta I library contains 15 billion sFv inserts; the Mehta II library contains 12 billion sFv inserts. Natural peptide libraries are known in the art. (See, Matthews et al., J. Immunol. 169(2): 837-46 (2002)). Preferably, a natural peptide library contains peptides from about 25 to about 200 amino acids in length, as this size peptide has been demonstrated to represent native epitopes. (See, Fack et al., J. Immunol. Methods 206:43 (1997); Matthews et al., J. Immunol. 169:837 (2002)). Random peptide libraries are known in the art and are available from BD Biosciences (San Jose, Calif.), New England Biolabs (Beverly, Mass.) and other commercial sources. Library inserts can be amplified and ligated into the viral display vectors of the invention. Alternatively, the inserts can be excised from the host library and ligated into the viral display vectors.

Immunoglobin Polypeptides

The fusion polypeptide further includes at least a region of a an immunoglobulin polypeptide. "At least a region" is meant to include any portion of an immunoglobulin molecule, such as the light chain, heavy chain, $F_c$ region, hinge region, CH1 region, CH2 region, CH3 region Fab region, Fv region or any fragment or combination thereof. Preferably, the immunoglobulin polypeptide contains the hinge region, the CH2 region and CH3 region of an IgG molecule (e.g., IgG1).

Transmembrane Moiety

A transmembrane moiety (or transmembrane domain) is a plurality of amino acids that is capable of extending across a biological membrane of a cell, such as the plasma membrane or a membrane of an organelle. A transmembrane moiety is a polypeptide capable of inserting into and remaining anchored within the viral capsid surface and/or the plasma membrane of a mammalian cell. When included in the fusion protein of the invention, the transmembrane moiety is capable of localizing the fusion protein to the viral capsid surface and/or to the plasma membrane of a mammalian cell. The transmembrane moiety is a viral transmembrane moiety, such as a lentiviral transmembrane moiety. Lentiviral transmembrane moieties include for example envelope polypeptide from HIV, SIV, CAEV, BIV, BLV, and FIV or a functional fragments thereof.

The HIV-1 gp160 envelope polypeptide is a polypeptide of about 856 amino acids (See Table 2; SEQ ID NO:1 and GenBank Accession numbers AAO40783, AAA76671, BAA12995, and P03377) that is proteolytically processed into a gp120 and a gp41 polypeptide. The amino acid sequence of an HIV-1 gp160 envelope polypeptide is provided as SEQ ID NO: 1 in Table 2. The gp41 polypeptide includes amino acids 512-856 of SEQ ID NO: 1 (See also, GenBank Accession No.: NP_057856). The transmembrane moiety of gp41 is generally located between about amino acids 675-715 of the gp160 polypeptide. Additional, lentiviral envelope proteins are provided by GenBank Accession numbers AAT41729 from SIV, P31627 from CAEV, P19557 from BIV, P03380 from BLV, and NP_040976 envelope from FIV.

TABLE 2

Polypeptide sequence of HIV-1 gp160 (SEQ ID NO:1)

mrvkekyqhlwrwgwrwgtmllgmlmicsateklwvtvyygvpvwkeatt tlfcasdakaydtevhnvwathacvptdpnpqevvlvnvtenfnmwkndm veqmhediislwdqslkpcvkltplcvslkctdlkndtntnsssgrmime kgeikncsfnistsirgkvqkeyaffykldiipidndttsykltscntsv itqacpkvsfepipihycapagfailkcnnktfngtgpctnvstvqcthg irpvvstqlllngslaeeevvirsvnftdnaktiivqlntsveinctrpn nntrkririqrgpgrafvtigkignmrqahcnisrakwnntlkqiasklr eqfgnnktiifkqssggdpeivthsfncggeffycnstqlfnstwfnstw stegsnntegsdtitlpcrikqiinmwqkvgkamyappisgqircssnit gllltrdggnsnneseifrpgggdmrdnwrselykykvvkieplgvaptk akrrvvqrekravgigalflgflgaagstmgaasmtltvqarqllsgivq qqnnllraieaqqhllqltvwgikqlqarilaverylkdqqllgiwgcsg klicttavpwnaswsnksleqiwnhttwmewdreinnytslihslieesq nqqekneqelleldkwaslwnwfnitnwlwyiklfimivgglvglrivfa vlsivnrvrqgysplsfqthlptprgpdrpegieeeggerdrdrsirlvn gslaliwddlrslclfsyhrlrdllllivtrivellgrrgwealkywwnll qywsqelknsavsllnataiavaegtdrvievvqgacrairhiprrirqg lerill Alternatively, the transmembrane moiety is a mammalian transmembrane moiety, such as CD28, CD8, or IgM transmembrane moiety or functional fragment.

As used herein, a "functional fragment" of a transmembrane moiety includes any portion or fragment of a transmembrane moiety that is sufficient to localize the fusion protein to the surface of the viral particle and/or to the mammalian cell plasma membrane. For example, a transmembrane domain includes the amino acid sequence NRVRQGYS (SEQ ID NO: 14) or GGTETSQVAPA (SEQ ID NO: 15).

Generally, transmembrane moieties have positively charged amino acids (such as lysine and arginine) at their ends and uncharged amino acids in the center. Transmembrane proteins are capable of having an N-terminal signal sequence that targets these polypeptides to the endoplasmic reticulum. Transmembrane moieties include polypeptide sequences having one or more alpha-helical structures. Usually, an alpha-helical transmembrane domain of 25 or more amino acids in length is sufficient to span the plasma membrane. Alternatively, the transmembrane moiety may include a polypeptide having one or more beta-barrel structures. An exemplary transmembrane moiety includes the transmembrane domain from gylcophorin A (Val-Gln-Leu-Ala-His-His-Phe-Ser-Glu-Pro-Glu-Ile-Thr-Leu-Ile-Ile-Phe-Gly-Val-Met-Ala-Gly-Val-Ile-Gly-Thr-Ile-Leu-Leu-Ile-Ser-Tyr-Gly-Ile; SEQ ID NO: 10). In some embodiments, transmembrane domains include polypeptide sequences having two or more β-sheets.

Transmembrane moieties include polypeptides provided in the TMbase of transmembrane proteins and their membrane-spanning domains. (See, K. Hofiann & W. Stoffel (1993), TMbase—A database of membrane spanning proteins segments. Biol. Chem. Hoppe-Seyler 374,166.) The TMbase database contains information from SwissProt and other database sources. Transmembrane moieties of the present invention include polypeptides identified using the TMpred program, which makes a prediction of membrane-spanning regions and their orientation using an algorithm based on the statistical analysis of the TMbase database of naturally occurring transmembrane proteins. Other programs capable of determining transmembrane domains in a polypeptide include GREASE, TMHMM, and TMAP.

Methods of Displaying a Candidate Polypeptide on a Viral Capsid

The viral display vector containing the nucleic acid encoding the fusion protein is introduced into a packaging cell. As used herein, the introduction of DNA into a cell is referred to as transduction, sometimes also known as transfection or infection.

Generally, the display vector is introduced by transfection in combination with one or more unlinked vectors, but one of skill in the art will appreciate that the methods of the invention can employ the use of other methods of introducing a nucleic acid vector into a recipient cell, including, but not limited to, microinjection. Preferred transfection means are calcium phosphate, FUGENE 6™ (Roche Diagnostics, Indianapolis, Ind.), and POLYFEC™ (Qiagen, Valencia, Calif.). The packaging cell is further transfected with a one, an envelope vector and a helper vector. The ratio of display vector:envelope vector: helper vector is about 2:1:2. Alternatively, the ratio of display vector:envelope vector: helper vector is about 1:2:1.

Following the introduction of the vector(s) into the packaging cell, the packaging cell generates one or more viral particles containing a nucleic acid encoding the fusion protein and the candidate polypeptide on the viral capsid. Optionally, the viral particles produced by the packaging cells are purified and/or concentrated by any means known to those skilled in the art. For example, viral particles expressing a nucleic acid encoding a selectable marker (e.g., eGFP) are then sorted by fluorescence assisted cell sorting (FACS) by detecting the expressed selectable marker. Alternatively, the viral particles are collected by filtration (e.g., filtration through a 0.45 μm and/or 0.22 μm filter) and pelleted by centrifugation at 100,000×g).

Viral particles having a candidate polypeptide or fragment thereof expressed on their surface can be used to identify those candidate polypeptides that bind to an antigen of interest (e.g., a "target antigen"). One or more viral particles, containing the fusion protein of the invention are contacted with a target antigen that has been tagged (e.g., a fluorescent tag such as FITC is attached chemically to the antigen). The viral particles are provided in solution. Alternatively, the viral particles are attached to a solid support. A solid support includes for example, a chip, a bead, paper or polystyrene The tagged target antigen contacts and binds the candidate polypeptide, and viral particles having a candidate polypeptide to which the target antigen has bound are selected by FACS or other suitable means known to those skilled in the art. The nucleic acid sequence encoding the candidate polypeptide may be sequenced, either directly or following amplification. In this way, the candidate polypeptide that binds to the target antigen can be identified.

Methods of Displaying a Candidate Polypeptide on the Surface of a Mammalian Cell The invention also provides methods for the display of a candidate polypeptide on the surface of a mammalian cells, which is useful, for example, to screen libraries containing polypeptides, antibodies or antibody fragments. It has recently been recognized that post-translational modifications such as N-linked and O-linked glycosylation, and sulfation. of polypeptides, e.g., antibodies play an important structural role. Thus, polypeptides produced by the methods of the invention will contain these post-translational modifications, while polypeptides produced in bacteria (e.g., using the method of phage display) will lack these post-translational modifications.

Candidate polypeptides are displayed on the surface of a mammalian cell by transfecting a packaging cell with the viral display vector containing the nucleic acid encoding the fusion protein as described above. Optionally, the nucleic acid encoding the fusion protein is expressed such that the candidate polypeptide is displayed on the surface of the viral capsid. However, those skilled in the art will recognize that expression of the fusion protein on the surface of the viral capsid is not necessary in order to achieve expression of the fusion protein on the surface of the mammalian cell.

Viral particles produced by the packaging cell are then contacted with a mammalian display cell, such that the mammalian display cell is infected by the viral particle. The viral particles are contacted with the mammalian cells at a multiplicity of infection (MOI) that will provide on average only 0-1 integrations per cell. For example, the viral particles are contacted with the mammalian cells at a multiplicity of infection of about 1. Generally, the viral vector is stably integrated into the mammalian cell. Alternatively, the integration is transient. The presence of the transmembrane moiety of the fusion polypeptide targets the expressed fusion protein to the surface of the mammalian cell such that the candidate polypeptide is displayed on the plasma membrane. Based upon the MOI, each mammalian cell will have a contain a unique nucleic acid encoding the fusion protein and thus a unique a candidate polypeptide on its surface. For example, if an antibody library used, (e.g., one or both of the Mehta libraries), to create the viral vector it should be possible to obtain 27 billion mammalian cells, each expressing a unique antibody on its cell surface.

Exemplary mammalian display cells include, BHK, VERO, HT1080, 293, 293T, RD, COS-7, CHO, Jurkat, HUT, SUPT, C8166, MOLT4/clone8, MT-2, MT-4, H9, PM1, CEM, myeloma cells (e.g., SB20 cells), and CEMX174 cell lines. Another exemplary mammalian display cells include the M12g3R (IgM+) B cell line. (See Rider et al., 2003 Science 301:213-15.)

The mammalian display cell is a cell line that is capable of constitutively mutating nucleic acids that are either stably or transiently transfected into the cell. (Cumbers et al., Nature Biotech 20:1129, (2002); and see editorial review form Presta, Nature Biotech. 20:1096(2002)). For example, the mammalian display cell is a Ramos Burkitt's lymphoma cell line, BL-2 cells, CL-01 cells (Martin et al., Nature 415:802, 2002) or chicken DT40 B-cell lymphoma cells (Sale et al., Nature 412:921, 2001). Alternatively, the mammalian cell to modified to overexpress activation-induced cytosine deaminase (AID) protein (Muramatsu, 2000; Di Noia, 2002; Petersen-Mahrt, 2002; Yoshikawa, 2002 and Gearhart, 2002 for brief editorial review), DNA polymerase iota (Faili, 2002) or other members of the family of TLS polymerases that are components of the immunoglobulin mutasome. The AID protein is required for the maturation of antibodies in mammals and other higher vertebrates, where it promotes somatic hypermutation (SHM), class switch recombination and gene conversion.

Mutation of the fusion polypeptide by the mammalian display cell results in a candidate polypeptide that has altered, increased or decreased, binding affinity an/or specificity for a target antigen of interest. For example, when the candidate polypeptide is an antibody or fragment thereof, mutation mimics the hypermutaton process of antibodies.

Optionally, the mammalian cells expressing a candidate polypeptide (i.e. infected cells) are separated (i.e. sorted) form the mammalian cell not expressing a candidate polypeptide. Sorting of infected mammalian cells allows uninfected cells to be removed from the population, which, in turn, reduces the incidence of non-specific binding interactions with labeled antigens. Moreover, when mammalian display cell is capable of mutating the nucleic acid as described above, sorting the cells recapitulates for example, the affinity maturation process of B cells during the in vivo immune response.

Infected mammalian cells are sorted by detecting a selectable marker such as eGFP. Alternatively, infected mammalian cells are sorted by identifying cells that bind an antigen. For example the cells are contacted with a labeled target antigen at a given concentration. The a labeled target antigen is combined with the mammalian cells in solution or on solid support. Solid supports include for example, a chip, bead, paper, plastic or other solid or semi-solid means. When the target antigen an mammalian cells are present in solution, FACS or other suitable selection means is used to identify the complex between bound antigen and candidate polypeptide to separate the bound complex from unbound tagged target antigens and unbound mammalian cells. In contrast, when the target antigen is on a solid support, column chromatography is used to separate mammalian cells presenting candidate polypeptide or antibody bound to tagged antigen. The antigen is bound to beads (e.g., cellulose or sepharose beads) in a chromatography column and a solution containing the mammalian cells is applied to the column. Unbound mammalian cells are removed from the column by one or more washing steps. The bound mammalian cells are then eluted from the column, such as with a high or low pH solution, a detergent solution, a high salt solution, or with chaotropic agents (e.g., urea and/or guanidine).

Preferably, the mammalian cells are sorted by both selectable marker expression and antigen binding.

Optionally, the infected mammalian cells are expanded in culture between sorting steps. The expansion may be clonal or non-clonal in nature. The amount of antigen used in the subsequent sorting steps is reduced. For example, the concentration of target antigen is reduced by 25%, 50%, 75%, 90%, 95%, 99%, 99.9%, 99.99% or 99.999%. Thus, in this way, the methods of the invention are used to identify candidate polypeptides that bind to the target antigen with higher specificity and affinity compared to the mean affinity of the candidate polypeptide prior to affinity selection process.

The nucleic acid sequence encoding the selected candidate polypeptide is determined. For example, the population of selected mammalian cells are lysed, such as with a detergent, and the nucleic acids encoding the candidate polypeptide are amplified by PCR and cloned into a suitable vector. Optionally, the amplified inserts are cloned into the lentiviral display vector and used to produce new virus particles, as described above. These particles can be used to infect additional mammalian cells, and the candidate polypeptide display method can be repeated one or more times.

The methods of the invention also allow for the production a soluble candidate polypeptide. Soluble candidate polypeptides are generated by excising the nucleic acid molecule encoding the transmembrane domain of the fusion protein following expression of the fusion protein on the surface of the viral particle or the mammalian cell. For example, these methods are useful for the localization of an antibody-producing cell to a target cell or tissue using the membrane anchored antibody, followed by delivery of a soluble antibody in vivo to specific cell type or tissue, such as a cancer cell. This soluble antibody may be cytotoxic, cytostatic, or induce apoptosis.

For example, a viral display vector described above may additionally contain two or more signal sites (or signal sequences), e.g., loxP sites, recognized by the Cre recombinase. The Cre-lox reaction functions as follows. P1 bacteriophage cyclization recombination (Cre) recombinase recognizes a pair of loxP binding sites flanking a nucleic acid molecule of interest. Here, the loxP sites can flank the nucleic acid sequence encoding the transmembrane moiety of the fusion protein. Optionally, nucleic acid sequences encoding one or more amino acids flanking the transmembrane moiety (termed "spacer amino acids") are provided. Spacer amino acids facilitate proper folding of the fusion protein. LoxP sites are 34 bp long and are composed of an 8 bp core, which determines directionality, flanked by 13 bp of palindromic (complementary) sequences. Sequences flanked by loxP sites are said to be "floxed". Cre enzyme brings together the two loxP sites, which carry complementary sequences. Depending on the orientation of the paired loxP sites, different results may be achieved. In the cre-lox system, nucleic acid sequences between two signal sites are deleted or inverted if the signal sites are on the same nucleic acid molecule. The intervening DNA may be excised or circularized, inverted or translocated. Optionally, the viral display vector also contains a nucleic acid sequence encoding cre recombinase. Cre expression can driven by an inducible promoter such as tetracycline/doxycycline. Optionally, loxP sites flank the nucleic acid sequence encoding cre recombinase in addition to flanking the transmembrane moiety of the fusion protein. The nucleic acid sequence encoding cre recombinase is positioned upstream (in a 5' direction) or downstream (in a 3' direction) relative to the loxP sites. The ability to induce cre recombinase expression provides the ability to produce soluble antibodies. The nucleic acid sequence encoding cre recombinase can be situated in a different vector, or has been stably integrated into the genome of the host cell.

Another example of a site-specific recombinase system is the flp system from yeast. The Flp recombinase is a 45 kD protein endoded by the 2 micron plasmid of the yeast *Saccharomyces cerevisiae*. A viral display vector described above may additionally contain two or more recombination targets (FRTs), recognized by the FLP recombinase. For example, two FRTs flank the nucleic acid sequence encoding the transmembrane moiety of the fusion protein.

A modified FLP recombinase with increased recombinase activity has also been described (See, Bucholz et al., Nature Biotech. 16, 657-662 (1998)). A suitable FRT sequence is: GAAGTTCCTATACTTTCTAGAGAATAG-GAACTTCGGAATAGGAACTTA (SEQ ID NO: 11). The FLP recombinase bind the FRTs, resulting in excision of the nucleic acid sequence encoding the transmembrane moiety and the production of a soluble antibody.

For example, a mammalian display cell that expresses an antibody that binds immunospecifically to a tumor specific antigen (TSA) on the surface of a cancer cell is identified using the mammalian cell antibody display methods of the invention. The antibody-producing mammalian cell is provided to a mammalian subject (e.g., a human subject having cancer or otherwise in need thereof), and the antibody on the surface of the mammalian cell homes in to the tumor antigen and binds specifically thereto. Detection and localization of the antibody producing cell is determined by the detection of expression of the detectable protein moiety. Once the antibody producing mammalian cell is co-localized with (and bound to) the cell displaying the tumor antigen, expression of the cre recombinase is induced (such as with chemical means, light, oxygen, or other inductive means) such that the recombinase removes the nucleic acid encoding the transmembrane moiety of the fusion protein. In the absence of the transmembrane domain, the fusion protein will be directed into the ER by the leader peptide and secreted outside the cell as a soluble antibody. These secreted soluble antibodies will then act locally upon the target tumor cell. Optionally, the antibody producing mammalian display cell also contains a nucleic acid encoding a toxin, which is also produced by the mammalian display cell. This toxin may be operably linked to the soluble antibody.

EXAMPLES

Example 1

Creation of Viral Display Vectors and Vector Systems

A viral display vector (outlined in FIG. 1) is constructed as follows. A nucleic acid molecule encoding a fusion protein is created by amplification of one or more candidate polypeptide-encoding inserts from a Mehta I/II library. Exemplary sFv inserts include "PS11", which is an sFv that binds immunospecifically to the TRM motif on human cyclinT1; "E46", which is an sFv that binds immunospecifically to the arginine-rich region of HIV-1 tat protein; "A8", which is an sFv that binds immunospecifically to the N-terminus of CCR5; and "anti-Tac", which is an sFv that binds immunospecifically to CD25 (the alpha chain of IL-2R). These inserts are ligated downstream of a nucleic acid sequence encoding an immunoglobulin leader protein and upstream of a nucleic acid sequence encoding an immunoglobulin molecule containing the hinge, CH2, and CH3 regions of human IgG1, such that, when the expressed nucleic acids are translated, the candidate polypeptide is operably connected to the leader polypeptide and the immunoglobulin molecule. Expression of the nucleic acid molecule is controlled by a CMV promoter. Downstream of the nucleic acid encoding the immunoglobulin molecule is a nucleic acid sequence encoding the transmembrane moiety from gp41. A nucleic acid molecule encoding enhanced green fluorescent protein (eGFP) is provided downstream of an IRES that is controlled by the CMV promoter.

Figure 4A:
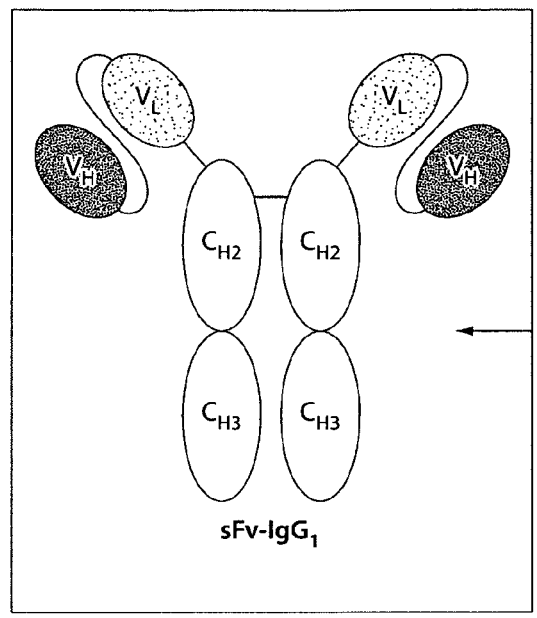
FIG. 4A is a schematic representation of a fusion protein of the invention containing an antibody.
Figure 4B:
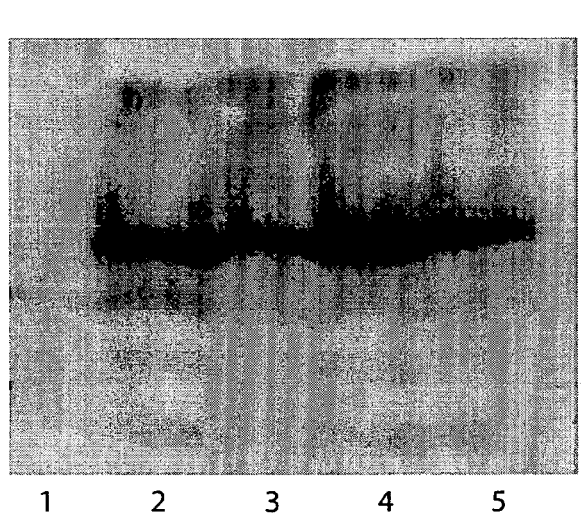
FIG. 4B is a photographic image of a Western blot demonstrating expression of fusion proteins of the invention in 293T cells.

Protein expression analysis of the viral display vectors is performed by transiently transfecting 293T cells using transfection means known to those skilled in the art, such as POLYFEC™ transfection reagent, then performing Western blot analysis using an antibody specific for gp41. As shown in FIG. 4B, the fusion proteins of the invention are expressed in transiently transfected 293T cells. Lane 1 shows mock transfected cells (no DNA added); lane 2 shows expression of a fusion protein containing the PS11 sFv; lane 3 shows expression of a fusion protein containing the PS11 sFv, wherein the gp41 transmembrane moiety is flanked on either end by a loxP sequence; lane 4 shows expression of a fusion protein containing the E46 sFv; and lane 5 shows expression of a fusion protein containing the E46 sFv, wherein the gp41 transmembrane moiety is flanked on either end by a loxP sequence.

The localization of the fusion proteins to the plasma membrane is confirmed using FACS analysis. For example, goat-anti-human IgG (γ-chain specific) PE conjugate is useful to detect the cell surface expression of the sFv-IgG-gp41 fusion proteins. Results of a typical FACS analysis are provided in Table 3.

TABLE 3

| Transfection | M1 % PE+ | M1 Mean F | M2 % PE+ | M2 Mean F |
|---|---|---|---|---|
| Mock transfection | 4.49 | 15.49 | 1.25 | 24.86 |
| HXBC2 + pTat (control vector) | 11.32 | 15.97 | 3.92 | 23.83 |
| PS11-gp41 | 37.25 | 19.85 | 19.12 | 27.12 |
| PS11-lox-gp41 | 28.99 | 21.64 | 11.01 | 37.27 |
| E46-gp41 | 34.88 | 18.76 | 13.65 | 29.33 |
| E46-lox-gp41 | 30.53 | 21.84 | 11.95 | 37.12 |

M1 = gate at 10; M2 = gate at 15

FACS analysis using fluorescently labeled antigens confirms that the fusion proteins expressed on the cell surface are capable of binding immunospecifically to target antigen. For example, biotinylated TRM peptide (2 mM, MW 4146.7, combined with Extravidin PE (Sigma E-4011)), was used in FACS experiments, the results of which are shown in Table 4. These results demonstrated that the PS11-containing fusion protein expressed on the surface of 293T cells is capable of binding to its target antigen.

The helper vector pCMVΔR8.2 and an envelope vector are also shown in FIG. 1. The helper vector contains the gag, pol, tat and rev genes under the control of an ieCMV promoter. The envelope vector contains the G protein of vesicular stomatitis virus ("VSV-G"), operably linked to the ieCMV promoter and A" (a polyadenylation sequence).

Example 2

Antibody Display on Viral Capsids

A population of viral display vectors containing sFv inserts from a Mehta I/II library are co-transfected with a helper vector and an envelope vector into 293T cells using $CaCl_2$ or POLYFEC™ transfection agent. Alternatively, a 293T cell line stably expressing VSV-g is used. To make fusion protein viral particles, 293T cells grown to 80%-100% confluence are transfected on a 10-cm plate with a transfection cocktail containing about 12 µg of viral display vector (1.0 µg/µl), about 12 µg of envelope vector (1.0 µg/µl), about 6 µg of helper vector pCMVΔR8.2 (0.5 µg/µt), 62 µl of 2M $CaCl_2$ in 2× HeBS. Viral particle-containing supernatant (the master viral stock) is collected at about 37, and 61 hours after transfection, filtered and stored at −80° C. Alternatively, the master viral stock is collected at 48, 72 and 96 hours after transfection. When required, viral particle supernatant is concentrated by centrifugation at 17,000 rpm in an SW28 rotor for 2 h. The pellet is resuspended in 1/10 volume media. Viral particles are sorted by fluorescence assisted cell sorting (FACS) by detecting the eGFP. The multiplicity of infection (moi) is determined by infecting 293T cells, followed by flow cytometric quantification of eGFP-positive cells. Incorporation of the fusion protein into viral particles is measured using Western analysis. Viral stocks are concentrated by centrifugation and contacted with SDS-PAGE loading buffer, then separated by PAGE, transferred to membranes and blotted with anti-gp41 or anti-human IgG.

Figure 4C:
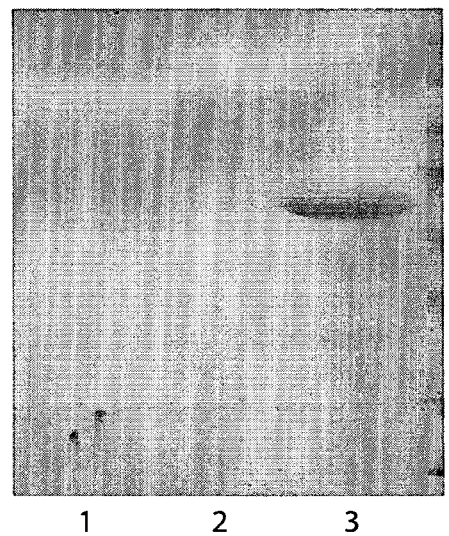
FIG. 4C is a photographic image of an SDS-PAGE demonstrating the captured antigens of a viral capture experiment using viral particles expressing an sFv on the viral capsid surface.
Figure 5A:
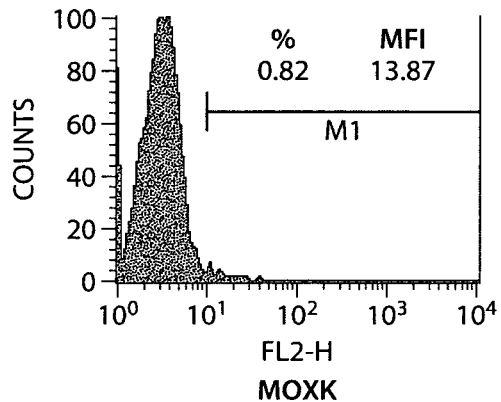
FIGS. 5A-H are a series of graphs demonstrating the detection of immunospecific binding of sFvTac-IgG1 antibodies to C8166-45 cells as measured by flow cytometry. MFI indicates mean fluorescence intensity. The amount of DNA used in each experiment is indicated below the graph.
Figure 5B:
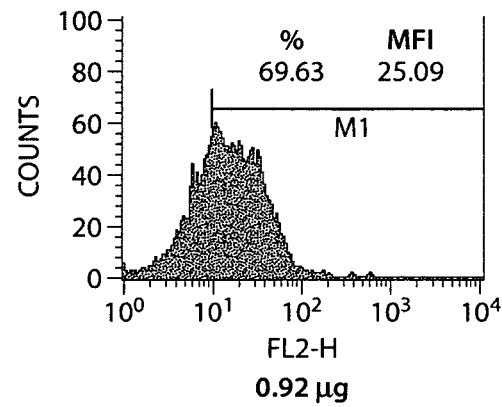
Figure 5C:
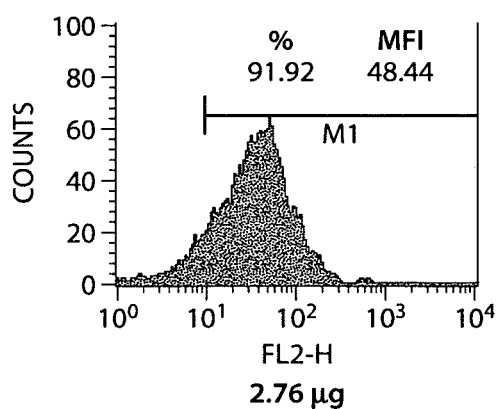
Figure 5D:
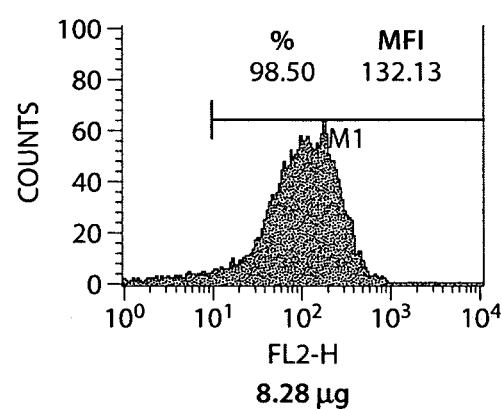
Figure 5E:
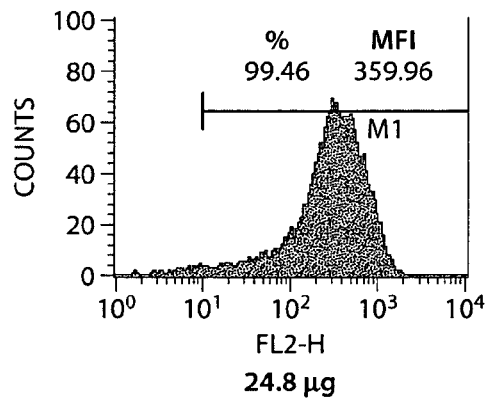
Figure 5F:
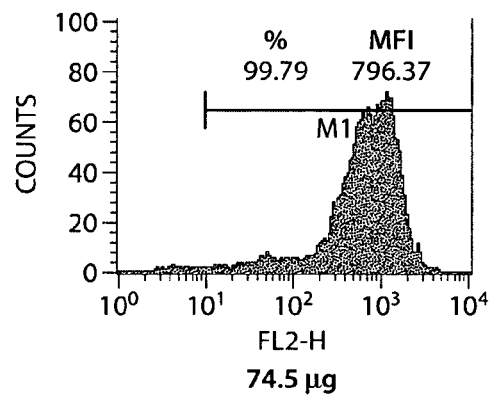
Figure 5G:
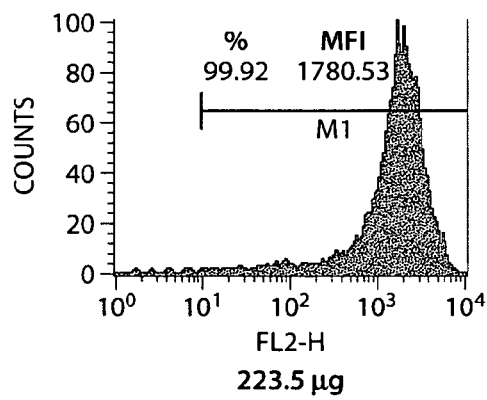
Figure 5H:
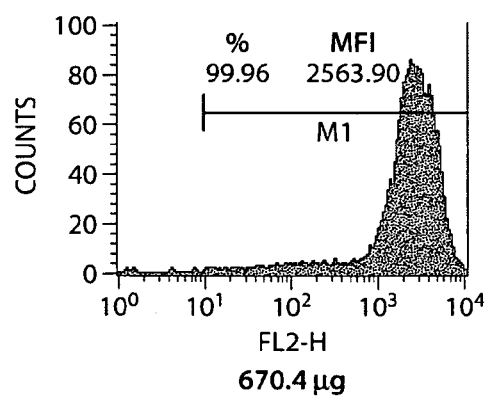
Figure 6:
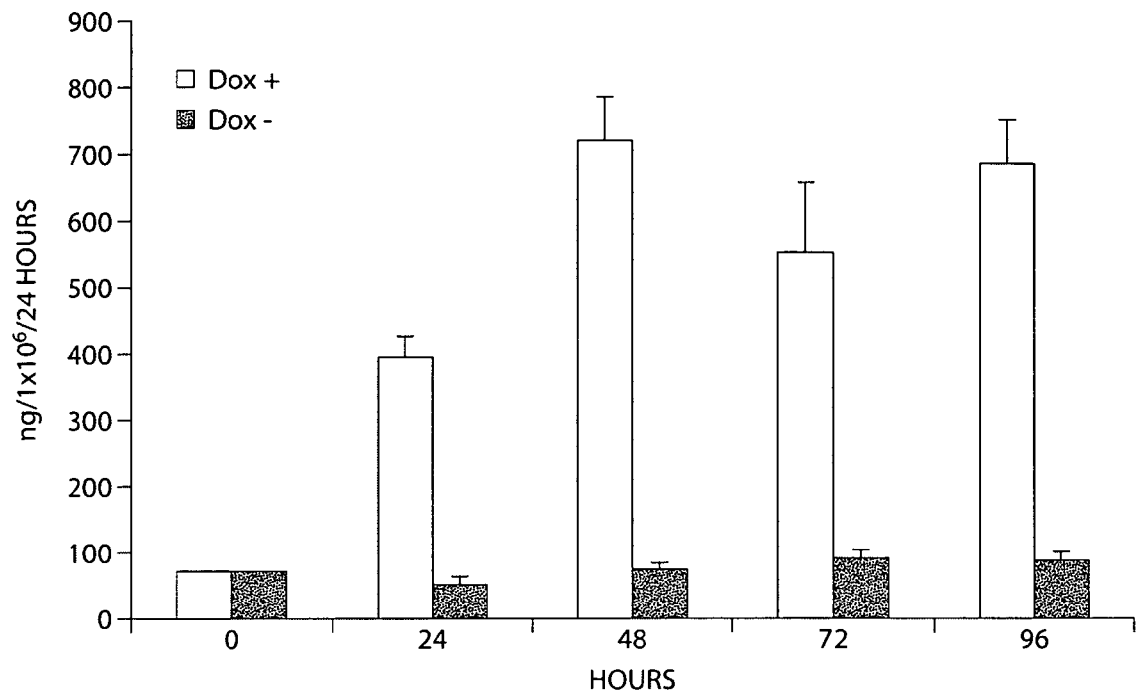
FIG. 6 is a bar graph demonstrating the induced expression of human single chain antibodies of the invention (sFvTac-IgG1) by doxycycline (Dox+) treatment, as compared to untreated cells (Dox−).
Figure 7:
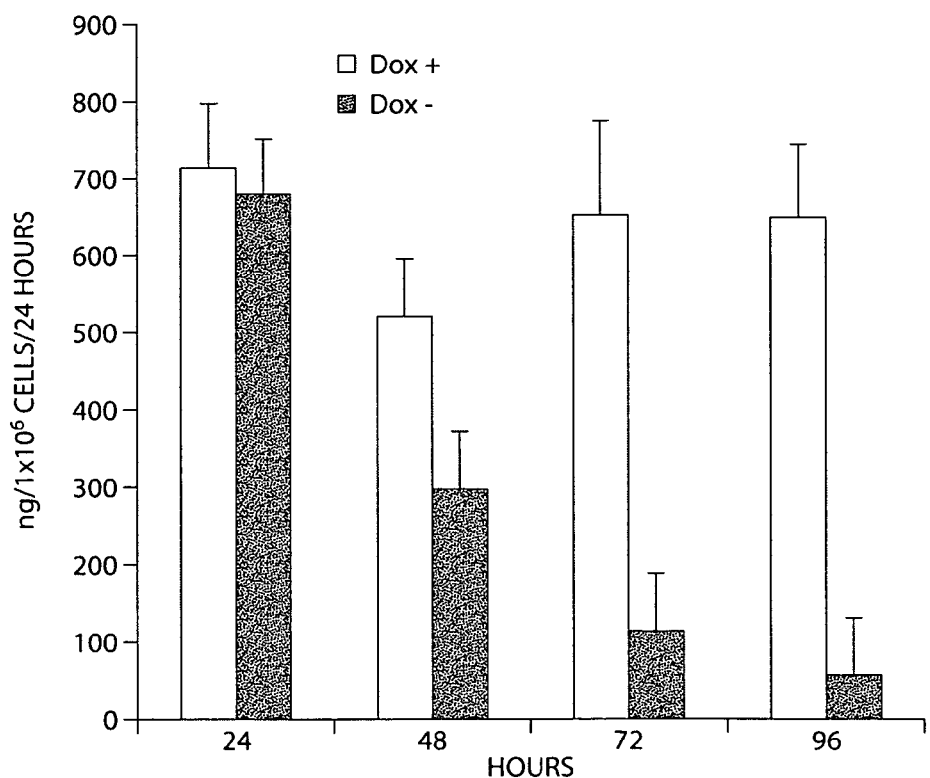
FIG. 7 is a bar graph demonstrating that the induction of human single chain antibodies of the invention (sFvTac-IgG1) following Dox treatment is reversible by removal of the drug.
Figure 8:
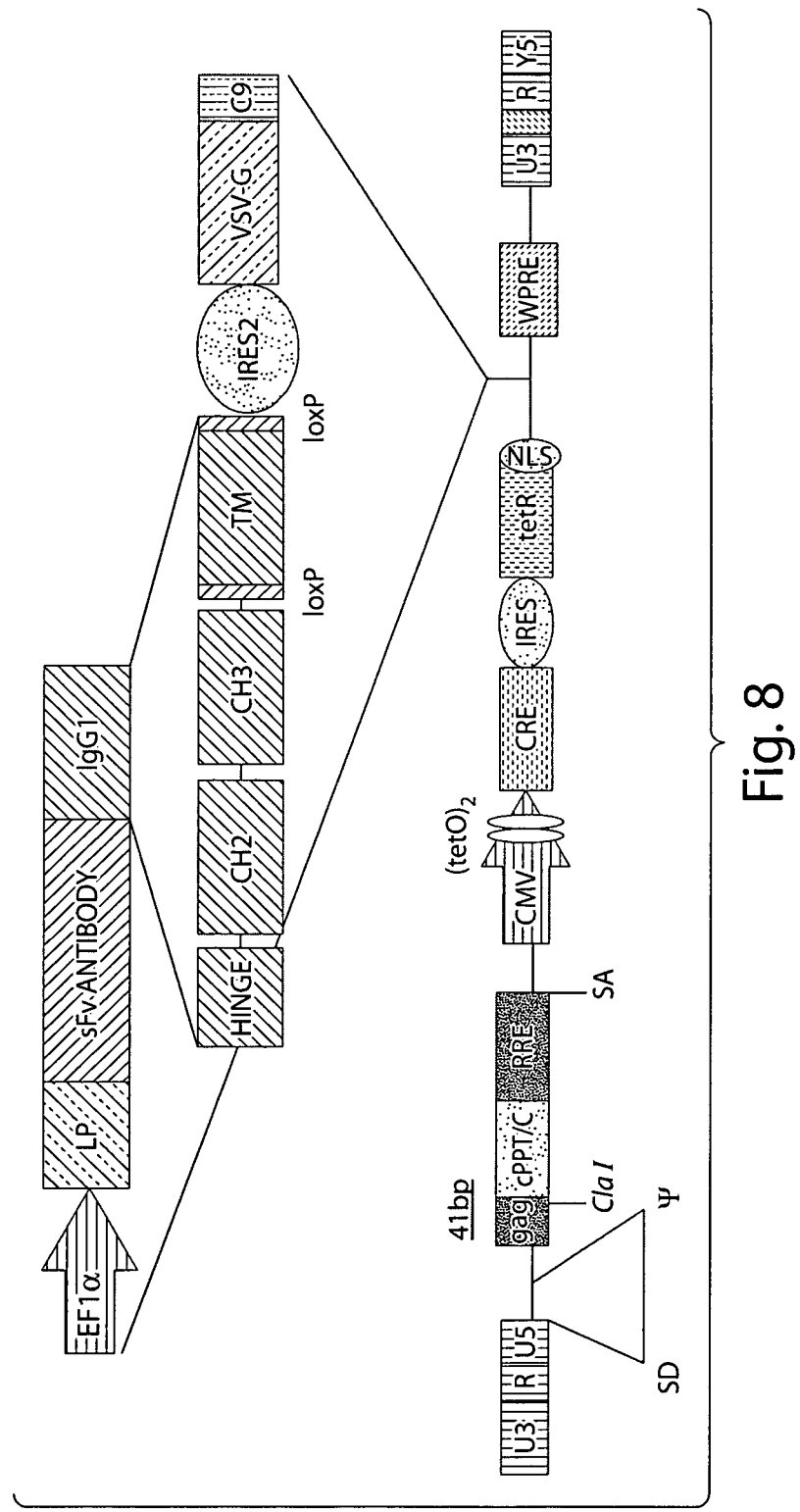
FIG. 8 is a schematic illustration of a lentiviral display vector containing cre recombinase and loxP sites.
Figure 9:
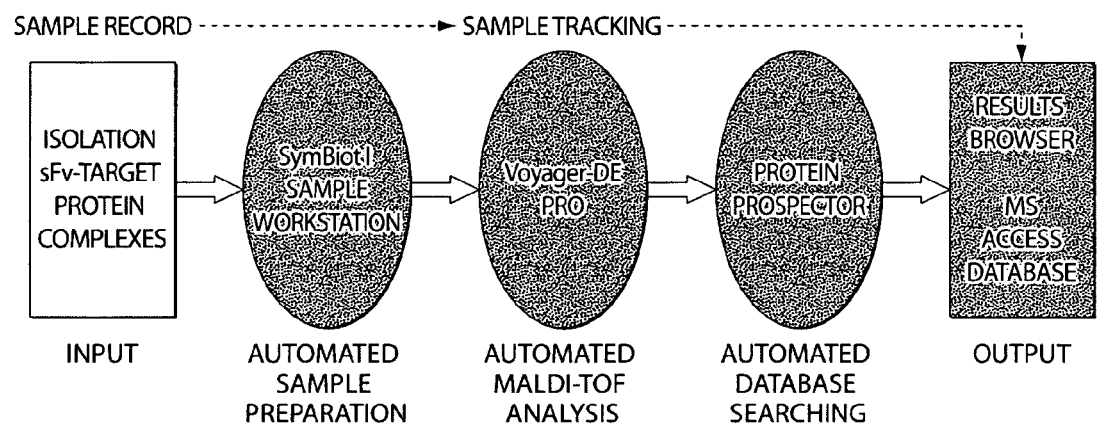
FIG. 9 is a schematic representation showing the identification of target proteins using a functional proteomics screen of the invention.
Figure 10:
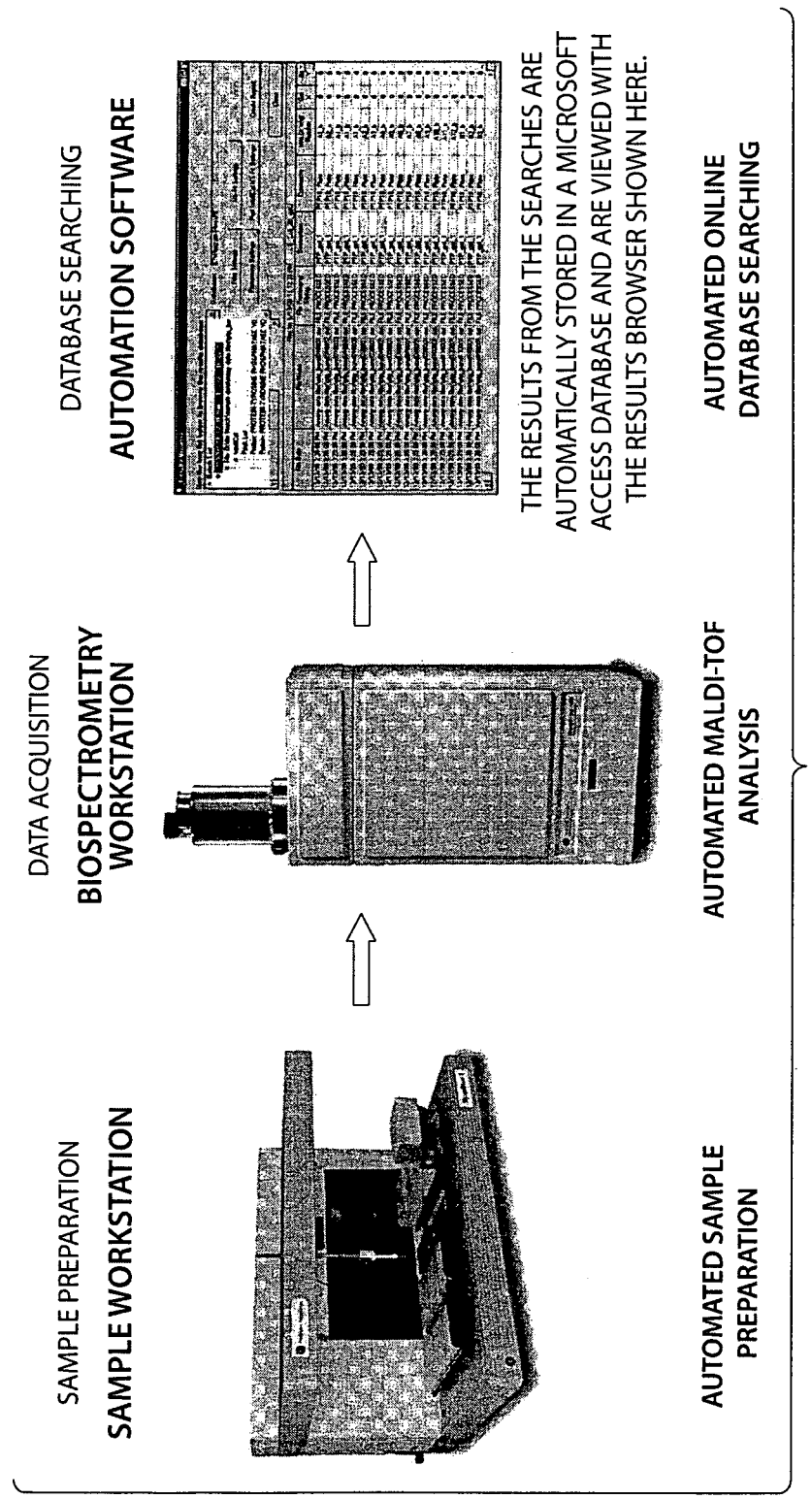
FIG. 10 is a schematic representation showing the creation of a database of the invention that is useful in functional proteomics.

Specific binding of the fusion protein to target antigen is demonstrated by viral particle capture experiments. Target antigens are coated on multiwell plates, blocked (such as with 1% BSA), and incubated with viral particles prepared as described above. Reverse transcriptase activity, an indication of specific binding of the fusion protein to the target antigen, is determined using $^3H$ and assigned a value (RT value). Results of a series of viral particle capture experiments is provided in Table 5, and demonstrates that lentiviral particles expressing PS11-containing fusion proteins bind specifically to their target antigens. Captured antigens were analyzed by SDS-PAGE and stained, as shown in FIG. 4C.

TABLE 4

|  | 1 uM | | 5 uM | | 25 uM | | 50 uM | |
|---|---|---|---|---|---|---|---|---|
| Transfection | % PE+ | MFI | % PE+ | MFI | % PE+ | MFI | % PE+ | MFI |
| Mock | 2.32 | 10.84 | 2.39 | 12.34 | 3.41 | 17.48 | 4.20 | 23.12 |
| PS11-gp41 | 15.76 | 13.17 | 19.82 | 12.95 | 20.58 | 13.62 | 26.31 | 14.85 |
| E46-gp41 | 4.61 | 10.24 | 5.06 | 10.53 | 6.73 | 13.08 | 9.55 | 15.92 |

M1 = gate at 7

TABLE 5

| | Hcyclin T1 antigens | | | | Control | | | | | |
|---|---|---|---|---|---|---|---|---|---|---|
| | 50 uM TRM peptide | | 3 ug GST-hCyclin T1-300 | | 3 ug Anti-human IgG-PE | | 3 ug GST | | 1% BSA | |
| Virus | 1 | 2 | 3 | 4 | 7 | 8 | 9 | 10 | 11 | 12 |
| PS11 10 ul* | 10250 | 16085 | 1765 | 1635 | 1095 | 1780 | 1225 | 920 | 500 | 900 |
| PS11 30 ul | 25955 | 32360 | 3675 | 5030 | 1135 | 95** | 1560 | 1770 | 360 | 4620 |
| E46 10 ul* | 1195 | 620 | 460 | 570 | 690 | 2065 | 1180 | 735 | 260 | 665 |
| E46 30 ul | 1230 | 1465 | 590 | 825 | 1055 | 2000 | 1245 | 980 | 555 | 1300 |
| CMV 10 ul* | 175 | 130 | 215 | 145 | 205 | 350 | 315 | 305 | 210 | 265 |
| CMV 30 ul | 300 | 230 | 125 | 155 | 220 | 240 | 255 | 165 | 120 | 160 |

*The total volume is equalized with addition of 20 ul media;
**did not have $^3$H mix

Example 3

Mammalian Cell Antibody Display

Figure 11:
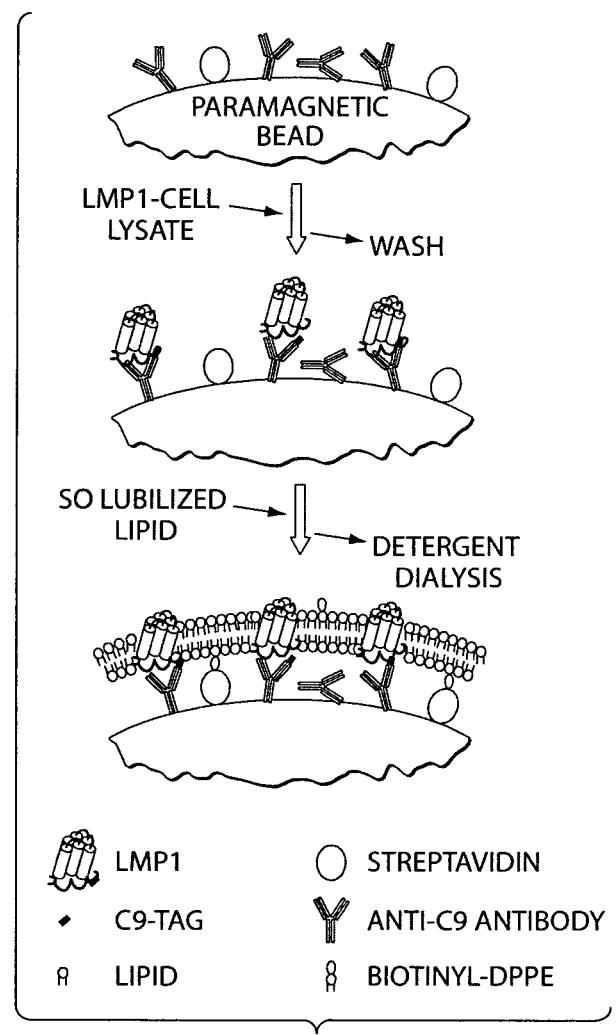
FIG. 11 is a schematic representation showing the use of paramagnetic proteoliposomes for the methods of lentiviral and/or mammalian display selection of the invention.

The master viral stock is contacted with a suspension of mammalian display cells overnight at an MOI of about 1. The mammalian cells are sorted by FACS on the basis of binding to an anti-Fc antibody or, alternatively, eGFP content. The sorted mammalian cells are contacted with target antigens that have been tagged. Suitable tags include FITC, streptavidin/biotin, and paramagnetic beads (See FIG. 11). The sorted mammalian cells having bound antigen are then selected. Following selection, the population of selected cells is expanded in culture for subsequent rounds of selection. Alternatively, nucleic acids are obtained from the population of selected cells and the nucleic acid encoding the candidate polypeptide is amplified and inserted into a display vector for one or more additional rounds of selection. To obtain the sequence of the candidate polypeptide of interest that binds to antigen, the selected cells are lysed and the nucleic acid sequences encoding the candidate polypeptides contained within the antigen-bound mammalian cells are cloned into a vector and then sequenced.

Experiments were performed to demonstrate the cell surface expression of fusion proteins on the surface of 293T mammalian display cells. 1×10$^6$ 293T cells were seeded on 6 well multiwell plates. The cells were co-transfected with two vectors, a vector expressing a fusion protein containing a candidate polypeptide of the invention, and a vector expressing GFP under the control of a CMV promoter, as shown in Table 6, using lipofectamine. About 48 hours after transfection, the transfected cells were harvested with 0.5 mM EDTA.

TABLE 6

| Sample | CMV-GFP | | % GFP | MFI | % APC | APC MFI |
|---|---|---|---|---|---|---|
| 1. Untransfected cells | | | 1.15 | 5.4 | 24.2 | 32 |
| 2. pCDNA3 | 4 µg | 0.2 µg | 98.5 | 1340 | 16.3 | 30 |
| 3. pCDNA3-CMV-PS11-Fc-gp41 | 4 µg | 0.2 µg | 45 | 551 | 90.65 | 261 |
| 4. pCDNA3-CMV-GFP | 4 µg | 0.2 µg | 99.66 | 3895 | 16 | 42 |
| 5. pCDNA3-CMV-PS11-Fc-C9-gp41(1-50) #10 | 4 µg | 0.2 µg | 99.5 | 1818 | 98.9 | 182 |
| 6. pCDNA3-CMV-PS11-Fc-C9-CD8 #7 | 4 µg | 0.2 µg | 97.7 | 1057 | 97.5 | 1523 |
| 7. pCDNA3-CMV-PS11-Fc-C9-gp41FL #1 | 4 µg | 0.2 µg | 50 | 241 | 96.8 | 196 |
| 8. pCDNA3-CMV-PS11-Fc-C9-CD28 #3 | 4 µg | 0.2 µg | 89.3 | 932 | 95.5 | 1660 |

Harvested transfected cells were analyzed for GFP expression and were stained with an anti-human Ig-APC conjugate to demonstrate Fc cell surface expression.

Sample 1 contains untransfected cells. Sample 2 contains the pcDNA vector with no insert. Sample 3 contains pcDNA3-CMV-PS11-Fc-gp41 without the C9 tag. Sample 4 contains a GFP control insert. Sample 5 contains a part of the lentiviral gp41 transmembrane region (corresponding to amino acids 1-50 of the TM region). Sample 6 contains the human CD8 transmembrane region. Sample 7 contains a full-length lentiviral gp41 transmembrane region. Sample 8 contains the human CD28 transmembrane region.

Figure 12A:
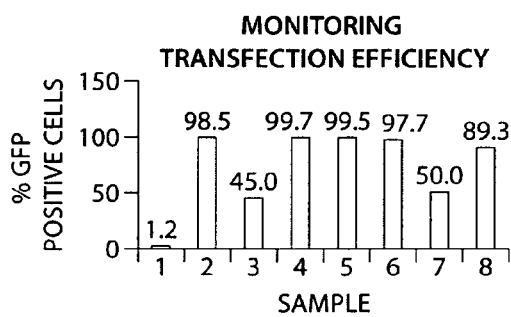
FIGS. 12A-D are a series of bar graphs demonstrating the cell surface expression of fusion proteins on the surface of 293T mammalian display cells co-transfected with a vector expressing a candidate polypeptide and a vector expressing GFP.
Figure 12B:
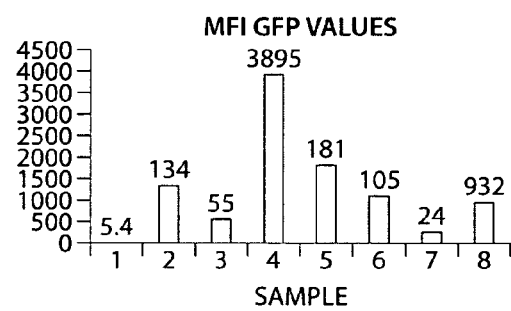
Figure 12C:
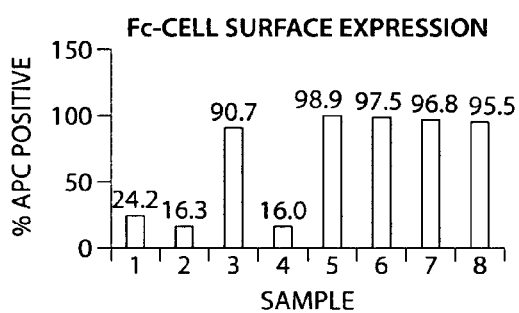
Figure 12D:
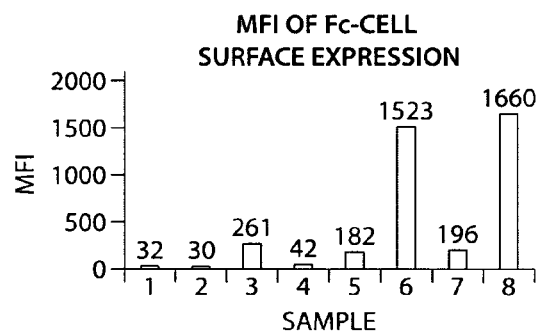

As shown in FIG. 12D, the CD8 and CD28 transmembrane regions result in robust targeting of the fusion protein to the surface of the display cells.

Additional experiments were performed to demonstrate the cell surface expression of fusion proteins on the surface of 293T mammalian display cells. 1×10$^6$ 293T cells were seeded on 6 well multiwell plates. The cells were co-transfected with a multi-functional vector containing an IRES, as shown in Table 7, using lipofectamine. About 48 hours after transfection, the transfected cells were harvested with 0.5 mM EDTA.

TABLE 7

| Sample | DNA | CMV-GFP | pCDNA3 | % GFP | MFI GFP | % APC |
|---|---|---|---|---|---|---|
| 1. Untransfected cells- APC stain | | | | 9.8 | 8 | 24.2 |
| 2. pSIN-delta gp41-CMV-GFP | 4 μg | 0.2 μg | | 99 | 3895 | 15.6 |
| 3. pSIN-mdeltaU3-CMV-PS11-Fc-gp41-IRES-ZsGreen-clone 3.4 | 4 μg | | 0.2 μg | 15 | 22 | 86.3 |
| 4. pSIN-mdeltaU3-CMV-PS11-Fc-gp41-IRES-GFP (#3) | 4 μg | | 0.2 μg | 12 | 12 | 88.2 |
| 5. pSIN-mdeltaU3-CMV-PS11-Fc-gp41-IRES-ZsGreen-clone #5 | 4 μg | | 0.2 μg | 86.1 | 139 | 90.3 |

Harvested transfected cells were analyzed for GFP expression and were stained with an anti-human Ig-APC conjugate to demonstrate $F_C$ cell surface expression.

Sample 1 contains untransfected cells. Sample 2 contains the pSIN vector expressing GFP under the control of a CMV promoter. Sample 3 contains pSIN-mdeltaU3-CMV-PS11-Fc-gp41-IRES-ZsGreen, where the IRES sequence was obtained from the pSIN-deltaU3-CMV-PS11-Fc-gp41-IRES-GFP vector. Sample 4 contains the pSIN-mdeltaU3-CMV-PS11-Fc-gp41-IRES-GFP, thereby expressing GFP. Sample 5 contains the pSIN-mdeltaU3-CMV-PS11-Fc-gp41-IRES-ZsGreen, where the IRES sequence was obtained from the IRES sequence originated from the HA-ZsGreens vector. In samples 3-5 the transmembrane region is the full length lentiviral gp41 transmembrane domain.

Figure 13A:
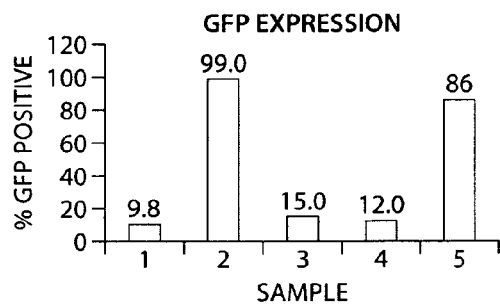
FIGS. 13A-D are a series of bar graphs demonstrating the cell surface expression of fusion proteins on the surface of 293T mammalian display cells transfected with a multi-functional vector containing an IRES.
Figure 13B:
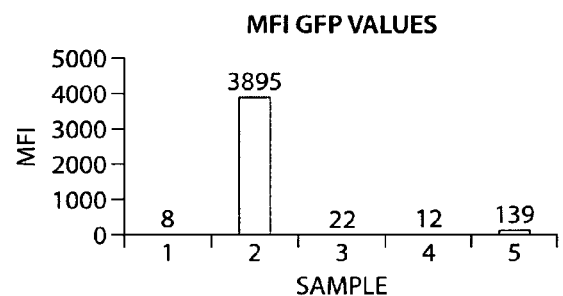
Figure 13C:
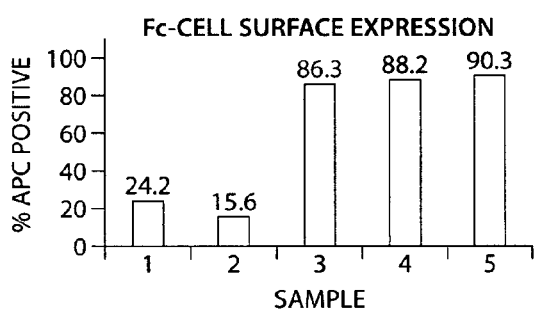
Figure 13D:
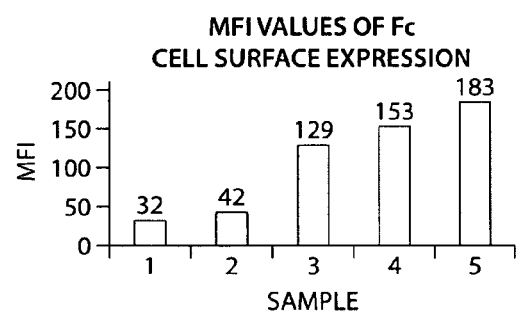

As shown in FIG. 13D, the multifunctional vectors of the present invention result in robust targeting of the fusion protein to the surface of the display cells.

Example 4

Affinity Selection of Human Antibodies

Selected antigen-bound mammalian cells are separated from unbound mammalian cells and expanded in culture to increase the number of mammalian cells producing a target antigen-specific antibody. The antibody display method of Example 4 is repeated with the concentration of target antigens reduced by 50%, 90%, 95%, 99%, 99.9%, 99.99% or more. For example, a antigen concentration of about 200 ng/ml is used in the first round of selection, and this concentration is reduced to about 1 ng/ml in a second round of selection.

Example 5

Affinity Maturation of Human Antibodies

It is desirable to identify candidate polypeptides, such as antibodies, that bind to a target antigen with very high specificity and very high binding affinity (low $K_d$). The present invention provides for the generation of high specificity antibodies by affinity maturation.

One method of affinity maturation involves the use of display cell lines that have a higher rate of mutation. An example of a mutation prone cell line is a lymphoma cell line, e.g., the Ramos Burkitt's lymphoma cell line. Mammalian cells expressing antibodies from mutated fusion proteins having increased affinity for the target antigen are selected using the display affinity selection methods described above in Example 4.

Another method of affinity maturation involves the induction of expression of a activation-induced cytosine deaminase (AID) protein in the display cells. Increased AID activity results in higher mutation rates in the candidate polypeptides. The viral display vector shown in FIG. 1 can be modified to include a nucleic acid molecule encoding the AID protein under the control of a promoter. Alternatively, the invention provides display cells having stably integrated the AID gene under the control of a constitutive or an inducible promoter.

Example 6

Induction of Antibody Expression

The viral display vector generated in Example 1 is modified by insertion of a tetR inducible element. Two tetO sequence concatamers are fused to the CMV minimal promoter. A tetR sequence is inserted downstream of the nucleic acid encoding the fusion protein of the invention. Thus, production of the fusion protein is regulated by addition of tetracycline.

Example 7

Quantitation of Antibody Cell Surface Expression using a C9 Tag

The present invention provides methods for determining the density of antibodies expressed on the surface of displaying mammalian cells. Quantitation of antibody cell surface expression allows for the determination of efficiency of antibody display, as well as the refinement of expression levels, e.g., by altering promoters and/or enhancers in the viral display vector.

Antibody cell surface expression quantitation is performed using a tag contained in the expressed fusion protein. Alternatively, quantitation is performed using labeled peptides (such as biotinylated peptides) that bind to single chain antibodies. Any tag capable of being detected with an entity that can be measured by any means (e.g., FACS) can be used in the present invention. One exemplary tag is the C9 peptide tag (GGTETSQVAPA, SEQ ID NO: 16). The C9 tag is recognized by the monoclonal antibody 1D4. Any means capable of detecting this antibody, such as FACS, can be used to quantitate expression levels. The C9 tag is located C terminal to the portion of immunoglobulin molecule and N terminal to the transmembrane moiety. In embodiments of the invention the C9 tag is connected to the portion of immunoglobulin molecule by a linker (e.g., a flexible linker such as SGGSS (SEQ ID NO: 17)). The C9 tag is linked to the C terminus of the linker by insertion of an XbaI site at the C terminus of the linker (which encodes the single amino acid arginine (R)). Exemplary viral display vectors containing the C9 linker are provided below in Table 8. The extracellular region of gp41 has 18 residues, the transmembrane region has 24 residues, and the intracellular region has 8 residues (the gp41 tag of SEQ ID NO: 14). Display vector 4 encodes a truncated gp41 polypeptide containing amino acids 1-50, while display vector 6 encodes the full length gp41 polypeptide. The extracellular region of CD8 has 12 residues, the transmembrane region has 21 residues, and the intracellular region ahs 11 residues (LYCNHRNRRRV; SEQ ID NO: 18). The extracellular region of CD28 has 39 residues, the transmembrane region has 27 residues, and the intracellular region has 13 residues. As a control, a pCDNA3 vector without the nucleic acid sequence encoding the fusion protein was used. scFv-48 is a single chain antibody against human CXCR4.

TABLE 8

| Viral display vector | DNA | % C9 Tag | MFI |
|---|---|---|---|
| 1. pCDNA 3 ID4 stain | 4 µg | 1.2 | 8.3 |
| 2. pCDNA3 - ID4 + anti Mouse FITC | 4 µg | 4.5 | 162 |
| 3. pCDNA3-scFv-48-C9-CD28 | 4 µg | 96 | 378 |
| 4. pCDNA3-CMV-PS11-Fc-C9-gp41(1-50) #10 | 4 µg | 97.7 | 515 |
| 5. pCDNA3-CMV-PS11-Fc-C9-CD8 #7 | 4 µg | 97 | 478 |
| 6. pCDNA3-CMV-PS11-Fc-C9-gp41FL #1 | 4 µg | 94 | 695 |
| 7. pCDNA3-CMV-PS11-Fc-C9-CD28 #3 | 4 µg | 97 | 470 |

Figure 14A:
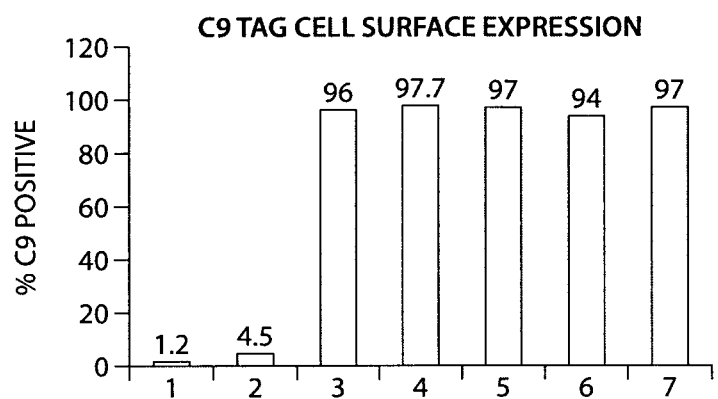
FIGS. 14A-B are a series of bar graphs demonstrating the cell surface expression of fusion proteins on the surface of 293T mammalian display cells detected with a C9 tag.
Figure 14B:
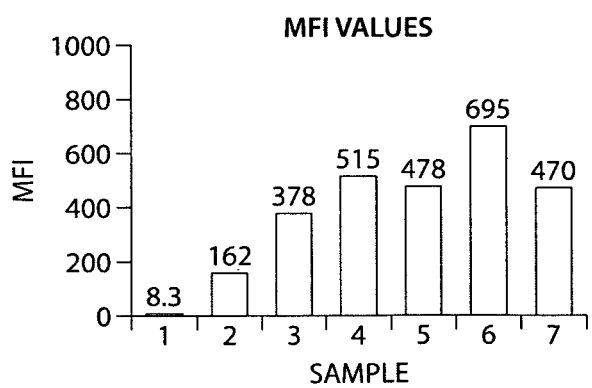
Figure 15A:
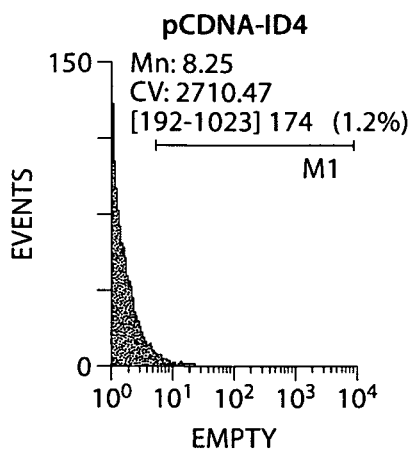
FIGS. 15A-G are a series of FACS analyses demonstrating the cell surface expression of fusion proteins on the surface of 293T mammalian display cells detected with a C9 tag.
Figure 15B:
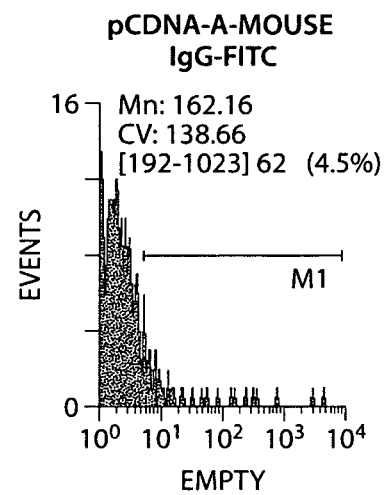
Figure 15C:
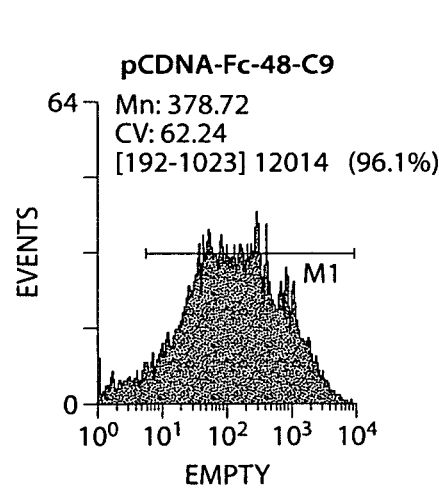
Figure 15D:
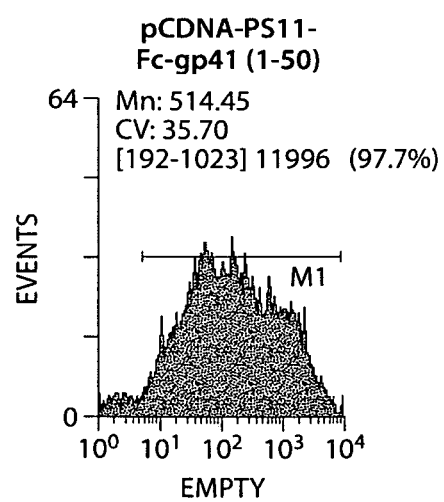
Figure 15E:
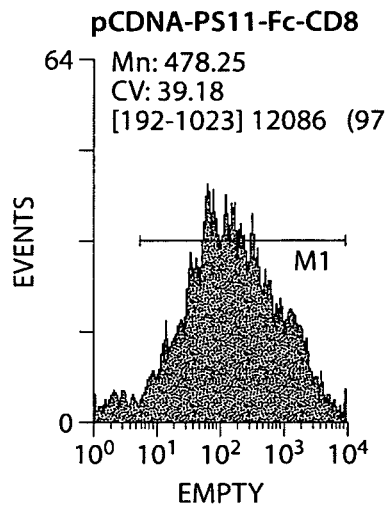
Figure 15F:
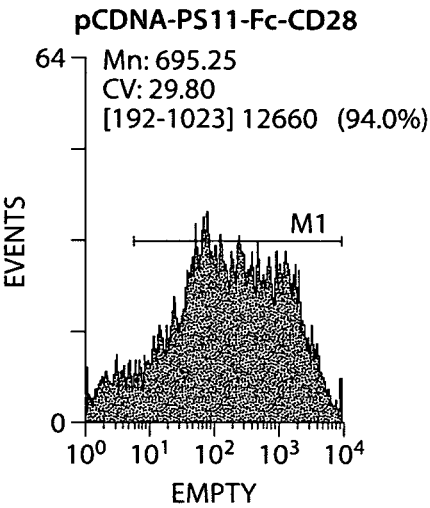
Figure 15G:
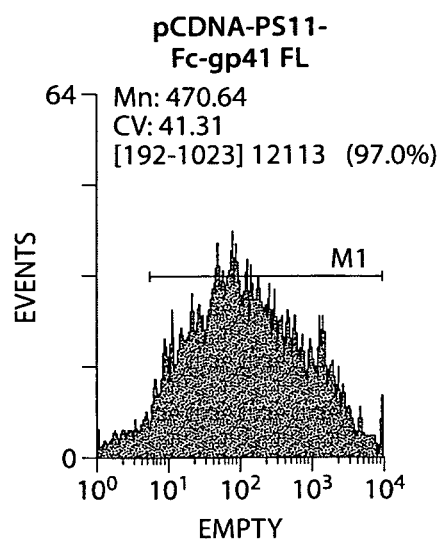

A typical antibody cell surface expression quantitation was performed as follows. 293T cells were seeded about 24 hours before transfection on 6 well plates ($1 \times 10^6$ cells per well). Viral display vector DNA (4 ug) was transfected using Lipofectamine 2000™. About 48 hours after transfection, cells were harvested for FACS analysis, using 0.5 mM EDTA. For antibody detection, a primary α-C9 antibody (ID4) was used at a concentration of 2 µl per $1 \times 10^5$ cells and a secondary α-mouse IgG-FITC labeled antibody was used at a 1:50 dilution. FACS analysis was performed as described above and known in the art. Results of this analysis are shown in FIGS. 14 and 15. FIG. 14A shows the percentage of cells that were positive for C9 tag expression as measured by FACS. The great majority (94% or more) of cells expressing fusion constructs containing C9 are identified using FACS, while very low levels of positive cells were seen in populations of cells transfected with control vectors lacking the C9 tag. FIG. 14B shows the mean fluorescence intensity (MFI) values for cells transfected with the viral display vectors listed in Table 8. The expression of fusion proteins containing either the truncated or full length gp41 polypeptide, and proteins containing either CD8 or CD28 transmembrane domains was quantitated by measuring MFI values in transfected cells. FIGS. 15A-G display the FACS plot for cells transfected with the viral display vectors described in Table 8.

Example 8

Figure 16:
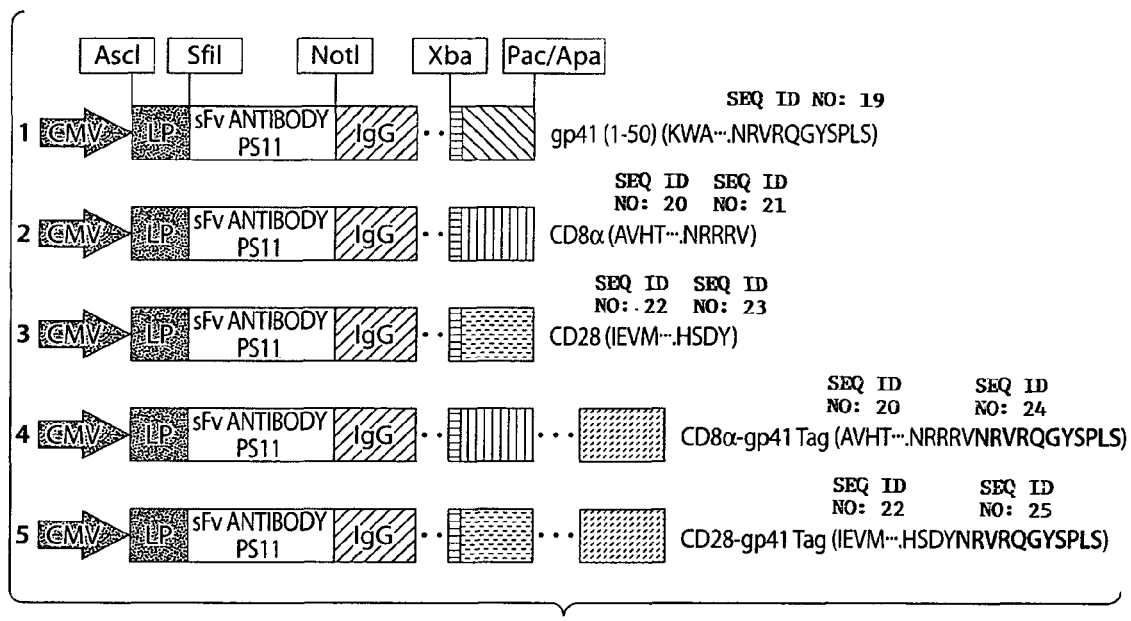
FIG. 16 is a schematic representation of exemplary fusion proteins.
Figure 17A:
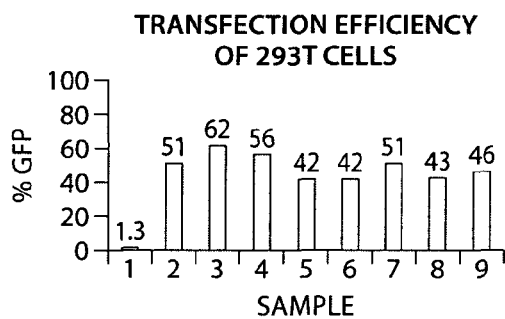
FIGS. 17A-D are a series of bar graphs demonstrating the transfection efficiency, MFI values, and cell surface expression of fusion proteins on the surface of 293T mammalian display cells.
Figure 17B:
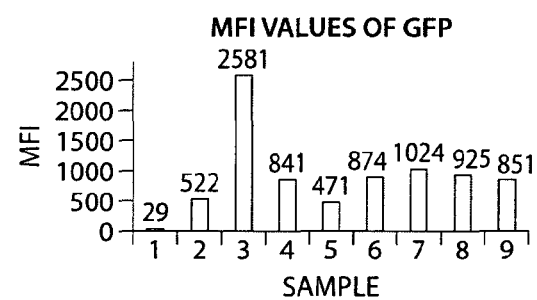
Figure 17C:
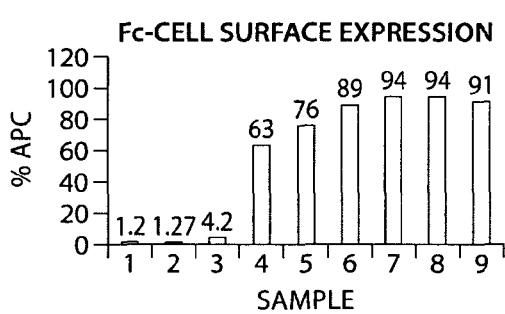
Figure 17D:
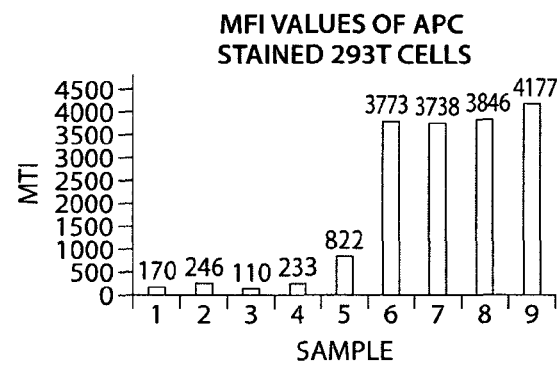
Figure 18A:
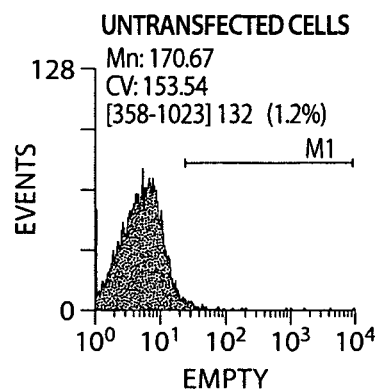
FIGS. 18A-I are a series of FACS analyses demonstrating the MFI values and cell surface expression of fusion proteins on the surface of 293T mammalian display cells stained with anti-human IgG.
Figure 18B:
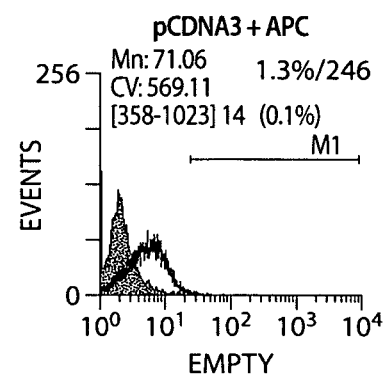
Figure 18C:
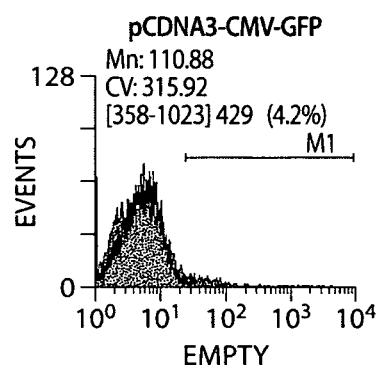
Figure 18D:
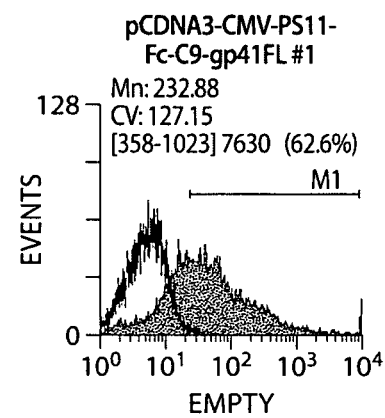
Figure 18E:
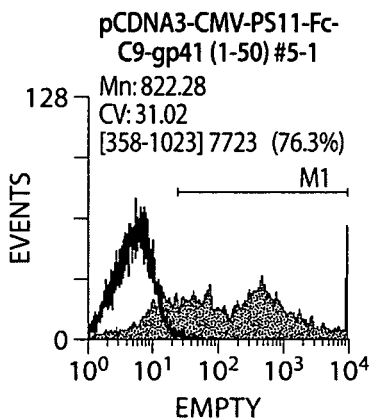
Figure 18F:
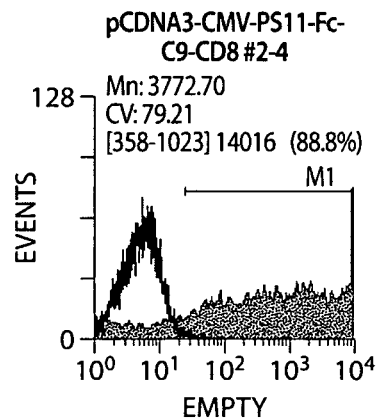
Figure 18G:
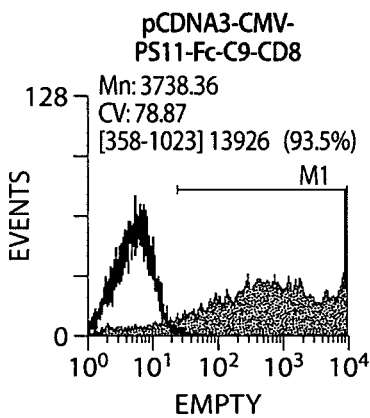
Figure 18H:
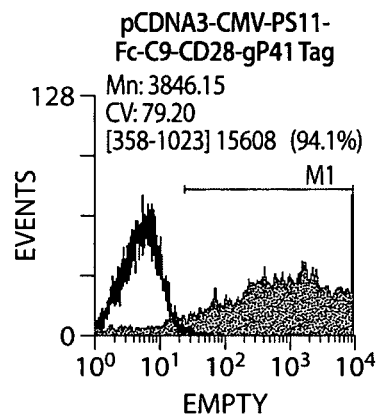
Figure 18I:
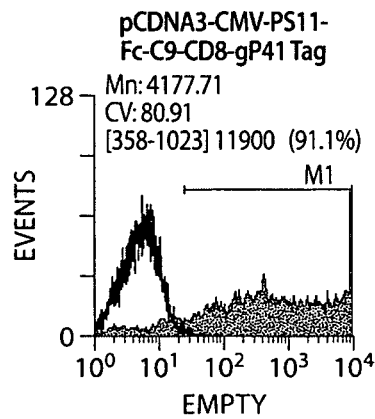
Figure 19A:
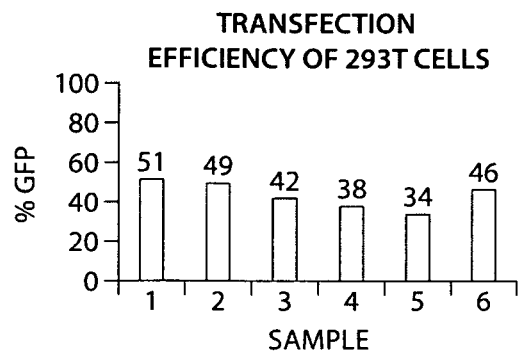
FIGS. 19A-D are a series of bar graphs demonstrating the transfection efficiency, MFI values, and cell surface expression of fusion proteins on the surface of 293T mammalian display cells.
Figure 19B:
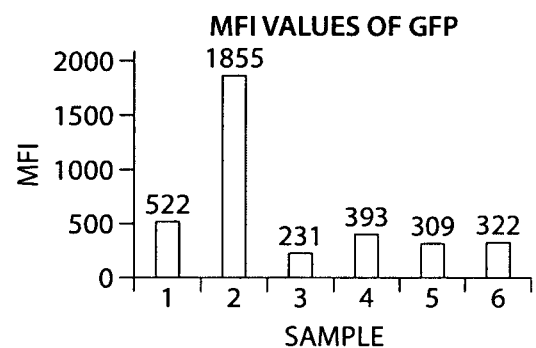
Figure 19C:
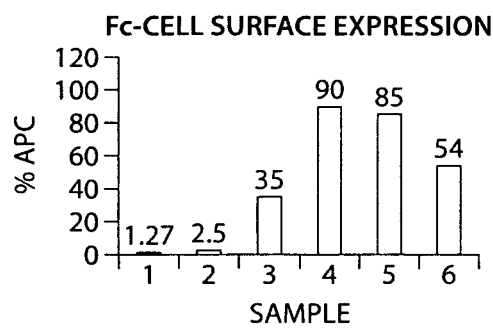
Figure 19D:
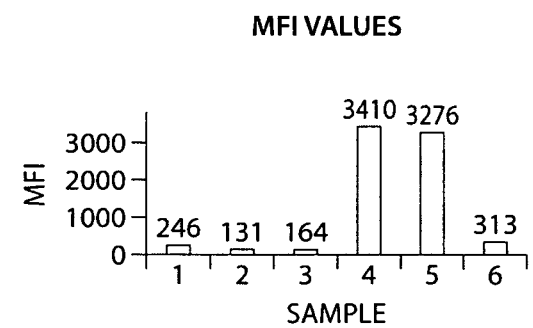
Figure 20A:
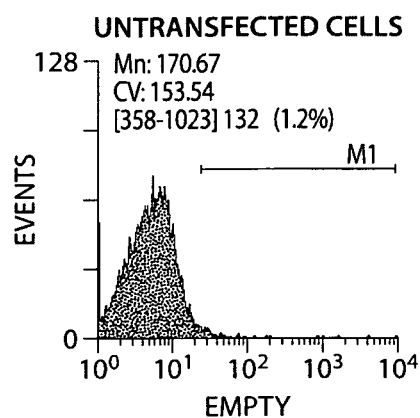
FIGS. 20A-G are a series of FACS analyses demonstrating the MFI values and cell surface expression of fusion proteins on the surface of 293T mammalian display cells stained with anti-human IgG.
Figure 20B:
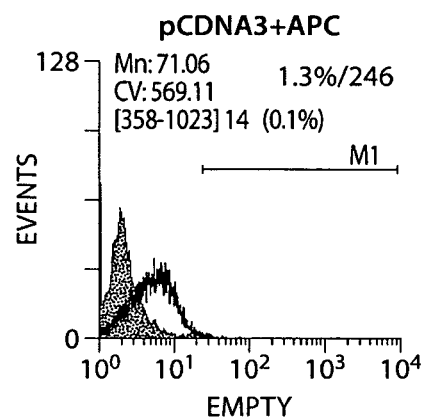
Figure 20C:
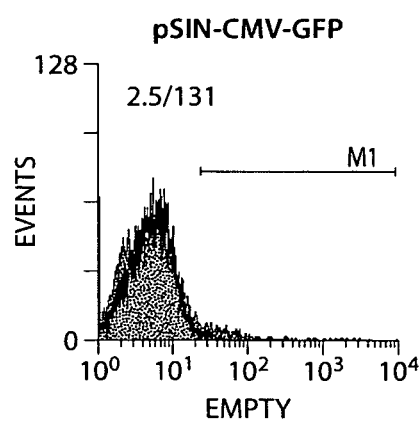
Figure 20D:
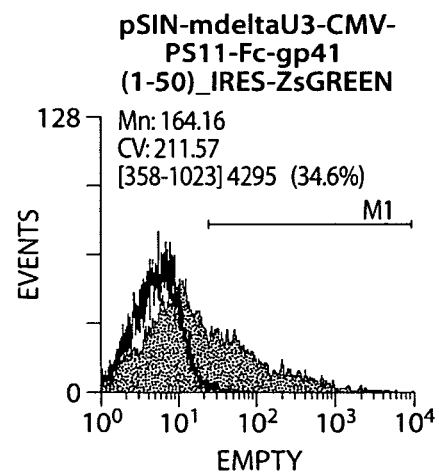
Figure 20E:
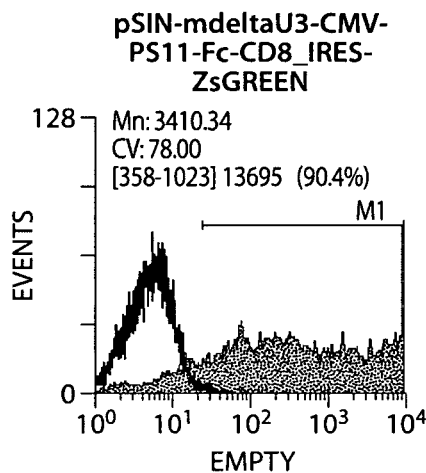
Figure 20F:
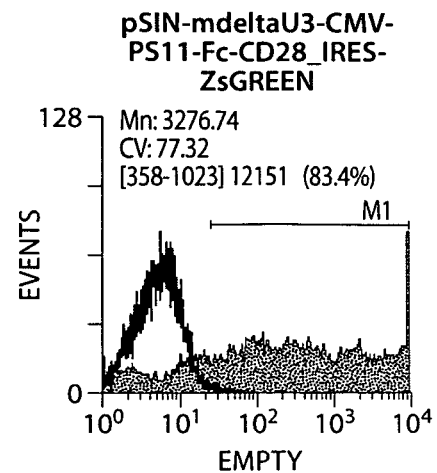
Figure 20G:
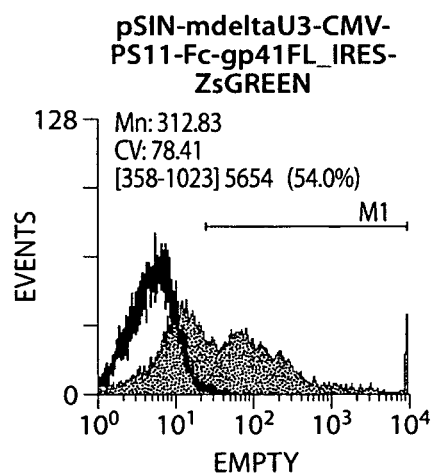

Quantitation of Antibody Cell Surface Expression in Constructs Containing Envelope Incorporation Signals The present invention provides fusion viral display vectors that contain the gp41 envelope (env) incorporation signal. FIG. 16 demonstrates several fusion protein constructs. Construct 1 contains amino acids 1-50 of the gp41 TM region. Construct 2 contains the CD8 transmembrane domain. Construct 3 contains the CD28 transmembrane domain. Construct 4 contains the CD8 transmembrane domain operably linked to the gp41 env incorporation signal. Construct 3 contains the CD28 transmembrane domain operably linked to the gp41 env incorporation signal. The constructs listed in Table 9 were transfected into 293T cells as follows. 293T cells were seeded on 6 well plates ($1 \times 10^6$/well). Cells were transfected using lipofectamine and 48 hours post transfection, cells were harvested with 5 mM EDTA and analyzed for GFP and Fc-surface expression using α-human-IgG-APC. Results are shown in FIGS. 17 and 18, and demonstrate that the CD8, CD28, and gp41 TM domains result in substantial cell surface expression of the transfected fusion protein; CD8 and CD28 in the presence of absence of the envelope incorporation signal, give higher levels of cell surface expression than gp41 TM.

TABLE 9

|  | CMV-GFP |  | % GFP | MFI | % APC | APC MFI |
|---|---|---|---|---|---|---|
| 1. Untransfected cells |  |  | 1.3 | 29 | 1.2 | 170 |
| 2. pCDNA3 + APC | 4 µg | 0.1 µg | 51 | 522 | 1.27 | 246 |
| 3. pCDNA3-CMV-GFP + APC | 4 µg | 0.1 µg | 62 | 2581 | 4.2 | 110 |
| 4. pCDNA3-CMV-PS11-Fc-C9-gp41FL #1 | 4 µg | 0.1 µg | 56 | 841 | 63 | 233 |
| 5. pCDNA3-CMV-PS11-Fc-C9-gp41(1-50) #5-1 | 4 µg | 0.1 µg | 42 | 471 | 76 | 822 |
| 6. pCDNA3-CMV-PS11-Fc-C9-CD8 #2-4 | 4 µg | 0.1 µg | 42 | 874 | 89 | 3773 |
| 7. pCDNA3-CMV-PS11-Fc-C9-CD28 #3-4 | 4 µg | 0.1 µg | 51 | 1024 | 94 | 3738 |
| 8. pCDNA3-CMV-PS11-Fc-C9-CD28-gp41 Tag #4-5 | 4 µg | 0.1 µg | 43 | 925 | 94 | 3846 |
| 9. pCDNA3-CMV-PS11-Fc-C9-CD8-gp41 Tag #6-5 | 4 µg | 0.1 µg | 46 | 851 | 91 | 4177 |

Example 9

Antibody Cell Surface Expression in Cells Transfected with Lentiviral Vectors

Viral display constructs (listed in Table 10) containing either truncated (amino acids 1-50) or full-length gp41 TM, CD8 TM or CD28 TM, were introduced into the pSIN lentiviral display vector to confirm the expression of the fusion proteins on the surface of mammalian cells. The lentiviral vectors contain a form of GFP, ZsGreen, to aid in detection, and were transfected into 293T cells as described above. Results are shown in FIGS. 19 and 20, and demonstrate that the viral display constructs contained in lentiviral vectors are efficiently expressed in 293T cells and result in cell surface expression of the fusion proteins.

TABLE 10

| DNA | CMV-GFP | pCDNA3 | % GFP | MFI GFP | % APC | MFI APC |
|---|---|---|---|---|---|---|
| 1. pCDNA3 + APC | 4 μg | 0.2 μg | | 51 | 522 | 1.27 | 246 |
| 2. pSIN-delta gp41-CMV-GFP | 4 μg | | | 49 | 1855 | 2.5 | 131 |
| 3. pSIN-mdeltaU3-CMV-PS11-Fc-gp41(1-50)-IRES-ZsGreen-clone 2A | 4 μg | | 0.2 μg | 42 | 231 | 35 | 164 |
| 4. pSIN-mdeltaU3-CMV-PS11-Fc-CD8-IRES-ZsGreen-clone 4A | 4 μg | | 0.2 μg | 38 | 393 | 90 | 3410 |
| 5. pSIN-mdeltaU3-CMV-PS11-Fc-CD28-IRES-ZsGreen-clone 5A | 4 μg | | 0.2 μg | 34 | 309 | 85 | 3276 |
| 6. pSIN-mdeltaU3-CMV-PS11-Fc-gp41 (FL)-IRES-ZsGreen-clone 5 | 4 μg | | 0.2 μg | 46 | 322 | 54 | 313 |

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims.

The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method of displaying a candidate polypeptide on the surface of a mammalian display cell, comprising the steps of:
   a) contacting a packaging cell with a viral display vector comprising a nucleic acid sequence encoding a fusion protein under conditions such that said packaging cell generates one or more viral particles comprising said nucleic acid sequence, wherein said fusion protein comprises:
      i) a leader peptide, wherein said leader peptide directs the fusion protein to the surface of said mammalian cell;
      ii) a candidate polypeptide;
      iii) at least a portion of an immunoglobulin molecule, wherein said portion comprises the hinge region, the CH2 region or the CH3 region of an IgG molecule or a combination thereof, and wherein said portion is not the candidate polypeptide;
      iv) a mammalian transmembrane moiety;
      v) an envelope incorporation signal; and
   b) contacting said viral particles with a mammalian display cell, wherein said mammalian display cell expresses said fusion protein and said candidate polypeptide is displayed on the surface of said mammalian display cell, and wherein said packaging cell further comprises an envelope vector comprising an env gene operably linked to a promoter and a polyadenylation sequence wherein said env gene encodes a functional envelope protein and a helper vector comprising one or more viral structural genes.

2. The method of claim 1, wherein said portion of an immunoglobulin molecule is further displayed on the surface of the mammalian display cell.

3. The method of claim 1, wherein said viral display vector is a lentiviral vector.

4. The method of claim 1, wherein said candidate polypeptide is an antibody or fragment thereof.

5. The method of claim 4, wherein said antibody is a single chain antibody, a domain antibody, a diabody, an Fab, an Fab' or an F(ab')2.

6. The method of claim 1, wherein said candidate polypeptide is derived from a library.

7. The method of claim 3, wherein said lentiviral vector is obtained from a lentivirus selected from the group consisting of human immunodeficiency virus (HIV), simian immunodeficiency virus (SIV), equine infectious anemia virus (EIAV), visna virus, caprine arthritis-encephalitis virus (CAEV), bovine immune deficiency virus (BIV), bovine leukemia virus (BLV), and feline immunodeficiency virus (FIV).

8. The method of claim 1, wherein said candidate polypeptide is expressed on the surface of said viral particles prior to contacting said viral particles with said mammalian display cell.

9. The method of claim 1, wherein said mammalian display cell is a Ramos Burkitt's lymphoma cell.

10. The method of claim 1, wherein said envelope incorporation signal comprises the gp41 envelope incorporation signal.

* * * * *

```
                        SEQUENCE LISTING

<160> NUMBER OF SEQ ID NOS: 25

<210> SEQ ID NO 1
<211> LENGTH: 856
<212> TYPE: PRT
<213> ORGANISM: Human immunodeficiency virus type 1

<400> SEQUENCE: 1

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220
```

-continued

```
Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
            275                 280                 285

Asn Thr Ser Val Glu Ile Asn Cys Thr Arg Pro Asn Asn Thr Arg
        290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
                340                 345                 350

Phe Gly Asn Asn Lys Thr Ile Ile Phe Lys Gln Ser Ser Gly Gly Asp
            355                 360                 365

Pro Glu Ile Val Thr His Ser Phe Asn Cys Gly Gly Glu Phe Phe Tyr
370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
            435                 440                 445

Ile Thr Gly Leu Leu Leu Thr Arg Asp Gly Gly Asn Ser Asn Asn Glu
450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
            515                 520                 525

Thr Met Gly Ala Ala Ser Met Thr Leu Thr Val Gln Ala Arg Gln Leu
530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
            595                 600                 605

Pro Trp Asn Ala Ser Trp Ser Asn Lys Ser Leu Glu Gln Ile Trp Asn
            610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
```

```
                     645                 650                 655
Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855

<210> SEQ ID NO 2
<211> LENGTH: 21
<212> TYPE: PRT
<213> ORGANISM: Rattus norvegicus

<400> SEQUENCE: 2

Met Glu Thr Asp Thr Leu Leu Leu Trp Val Leu Leu Leu Trp Val Pro
1               5                   10                  15

Gly Ser Thr Gly Asp
            20

<210> SEQ ID NO 3
<211> LENGTH: 11
<212> TYPE: PRT
<213> ORGANISM: Bacteriophage T7

<400> SEQUENCE: 3

Met Ala Ser Met Thr Gly Gly Gln Gln Met Gly
1               5                   10

<210> SEQ ID NO 4
<211> LENGTH: 6
<212> TYPE: PRT
<213> ORGANISM: Rattus norvegicus

<400> SEQUENCE: 4

Val Val Val Val Val
1               5

<210> SEQ ID NO 5
```

-continued

```
<211> LENGTH: 18
<212> TYPE: PRT
<213> ORGANISM: Rattus norvegicus

<400> SEQUENCE: 5

Met Lys Trp Val Thr Phe Leu Leu Leu Leu Phe Ile Ser Gly Ser Ala
1               5                   10                  15

Phe Ser

<210> SEQ ID NO 6
<211> LENGTH: 22
<212> TYPE: PRT
<213> ORGANISM: Mus musculus

<400> SEQUENCE: 6

Met Asp Met Arg Ala Pro Ala Gln Ile Phe Gly Phe Leu Leu Leu Leu
1               5                   10                  15

Phe Pro Gly Thr Arg Cys
            20

<210> SEQ ID NO 7
<211> LENGTH: 18
<212> TYPE: PRT
<213> ORGANISM: Gallus gallus

<400> SEQUENCE: 7

Met Arg Ser Leu Leu Ile Leu Val Leu Cys Phe Leu Pro Leu Ala Ala
1               5                   10                  15

Leu Gly

<210> SEQ ID NO 8
<211> LENGTH: 17
<212> TYPE: PRT
<213> ORGANISM: Torpedo marmorata

<400> SEQUENCE: 8

Met Val Leu Thr Leu Leu Leu Ile Ile Cys Leu Ala Leu Glu Val Arg
1               5                   10                  15

Ser

<210> SEQ ID NO 9
<211> LENGTH: 12
<212> TYPE: PRT
<213> ORGANISM: Unknown Organism
<220> FEATURE:
<223> OTHER INFORMATION: signal peptide
<220> FEATURE:
<221> NAME/KEY: VARIANT
<222> LOCATION: (1)..(1)
<223> OTHER INFORMATION: Wherein Xaa is any amino acid
<220> FEATURE:
<221> NAME/KEY: VARIANT
<222> LOCATION: (12)..(12)
<223> OTHER INFORMATION: Wherein Xaa is any one or more amino acids or
      not present

<400> SEQUENCE: 9

Xaa Leu Leu Leu Val Gly Ile Leu Phe Trp Ala Xaa
1               5                   10

<210> SEQ ID NO 10
<211> LENGTH: 34
<212> TYPE: PRT
<213> ORGANISM: Homo sapiens
```

```
<400> SEQUENCE: 10

Val Gln Leu Ala His His Phe Ser Glu Pro Glu Ile Thr Leu Ile Ile
1               5                   10                  15

Phe Gly Val Met Ala Gly Val Ile Gly Thr Ile Leu Leu Ile Ser Tyr
            20                  25                  30

Gly Ile

<210> SEQ ID NO 11
<211> LENGTH: 48
<212> TYPE: DNA
<213> ORGANISM: Artificial Sequence
<220> FEATURE:
<223> OTHER INFORMATION: recombination target sequence

<400> SEQUENCE: 11
gaagttccta tactttctag agaataggaa cttcggaata ggaactta              48

<210> SEQ ID NO 12
<211> LENGTH: 33
<212> TYPE: DNA
<213> ORGANISM: Artificial Sequence
<220> FEATURE:
<223> OTHER INFORMATION: sequence containing loxP sites

<400> SEQUENCE: 12
ataacttcgt atagcataca ttatacgaag tta                              33

<210> SEQ ID NO 13
<211> LENGTH: 11
<212> TYPE: PRT
<213> ORGANISM: Unknown Organism
<220> FEATURE:
<223> OTHER INFORMATION: polypeptide expressed from a sequence
      containing loxP sites

<400> SEQUENCE: 13

Ile Thr Ser Tyr Ser Ile His Tyr Thr Lys Leu
1               5                   10

<210> SEQ ID NO 14
<211> LENGTH: 8
<212> TYPE: PRT
<213> ORGANISM: Human immunodeficiency virus type 1

<400> SEQUENCE: 14

Asn Arg Val Arg Gln Gly Tyr Ser
1               5

<210> SEQ ID NO 15
<211> LENGTH: 11
<212> TYPE: PRT
<213> ORGANISM: Mus musculus

<400> SEQUENCE: 15

Gly Gly Thr Glu Thr Ser Gln Val Ala Pro Ala
1               5                   10

<210> SEQ ID NO 16
<211> LENGTH: 11
<212> TYPE: PRT
<213> ORGANISM: Mus musculus

<400> SEQUENCE: 16

Gly Gly Thr Glu Thr Ser Gln Val Ala Pro Ala
```

```
1               5                   10

<210> SEQ ID NO 17
<211> LENGTH: 5
<212> TYPE: PRT
<213> ORGANISM: Artificial Sequence
<220> FEATURE:
<223> OTHER INFORMATION: linker for connecting peptide tag to
      immunoglobulin

<400> SEQUENCE: 17

Ser Gly Gly Ser Ser
1               5

<210> SEQ ID NO 18
<211> LENGTH: 11
<212> TYPE: PRT
<213> ORGANISM: Homo sapiens

<400> SEQUENCE: 18

Leu Tyr Cys Asn His Arg Asn Arg Arg Arg Val
1               5                   10

<210> SEQ ID NO 19
<211> LENGTH: 11
<212> TYPE: PRT
<213> ORGANISM: Human immunodeficiency virus type 1

<400> SEQUENCE: 19

Asn Arg Val Arg Gln Gly Tyr Ser Pro Leu Ser
1               5                   10

<210> SEQ ID NO 20
<211> LENGTH: 4
<212> TYPE: PRT
<213> ORGANISM: Unknown Organism
<220> FEATURE:
<223> OTHER INFORMATION: fusion protein

<400> SEQUENCE: 20

Ala Val His Thr
1

<210> SEQ ID NO 21
<211> LENGTH: 5
<212> TYPE: PRT
<213> ORGANISM: Unknown Organism
<220> FEATURE:
<223> OTHER INFORMATION: fusion protein

<400> SEQUENCE: 21

Asn Arg Arg Arg Val
1               5

<210> SEQ ID NO 22
<211> LENGTH: 4
<212> TYPE: PRT
<213> ORGANISM: Unknown Organism
<220> FEATURE:
<223> OTHER INFORMATION: fusion protein

<400> SEQUENCE: 22

Ile Glu Val Met
1

<210> SEQ ID NO 23
```

```
<211> LENGTH: 4
<212> TYPE: PRT
<213> ORGANISM: Unknown Organism
<220> FEATURE:
<223> OTHER INFORMATION: fusion protein

<400> SEQUENCE: 23

His Ser Asp Tyr
1

<210> SEQ ID NO 24
<211> LENGTH: 16
<212> TYPE: PRT
<213> ORGANISM: Human immunodeficiency virus type 1

<400> SEQUENCE: 24

Asn Arg Arg Arg Val Asn Arg Val Arg Gln Gly Tyr Ser Pro Leu Ser
1               5                   10                  15

<210> SEQ ID NO 25
<211> LENGTH: 15
<212> TYPE: PRT
<213> ORGANISM: Human immunodeficiency virus type 1

<400> SEQUENCE: 25

His Ser Asp Tyr Asn Arg Val Arg Gln Gly Tyr Ser Pro Leu Ser
1               5                   10                  15
```